(12) United States Patent
Perret et al.

(10) Patent No.: US 9,023,836 B2
(45) Date of Patent: May 5, 2015

(54) USE OF SUBSTITUTED HETEROCYCLIC COMPOUNDS TO CONTROL SEA LICE ON FISH

(75) Inventors: Jean-Luc Perret, Neuchatel (CH); David Blaser, Basel (CH); Steve Nanchen, Basel (CH)

(73) Assignee: Novartis Tiergesundheit AG, Basel (CH)

(*) Notice: Subject to any disclaimer, the term of this patent is extended or adjusted under 35 U.S.C. 154(b) by 0 days.

(21) Appl. No.: 13/805,206

(22) PCT Filed: Jun. 15, 2011

(86) PCT No.: PCT/EP2011/059898
§ 371 (c)(1),
(2), (4) Date: Dec. 18, 2012

(87) PCT Pub. No.: WO2011/157733
PCT Pub. Date: Dec. 22, 2011

(65) Prior Publication Data
US 2013/0095126 A1    Apr. 18, 2013

(30) Foreign Application Priority Data
Jun. 18, 2010 (CH) .................................. 1001/10

(51) Int. Cl.
*A01N 43/80* (2006.01)
*A61K 31/506* (2006.01)
*A61K 39/00* (2006.01)
*A61K 31/4439* (2006.01)
*A61K 31/42* (2006.01)
*A61K 31/422* (2006.01)
*A61K 45/06* (2006.01)

(52) U.S. Cl.
CPC ................. *A61K 31/42* (2013.01); *A01N 43/80* (2013.01); *A61K 31/422* (2013.01); *A61K 31/4439* (2013.01); *A61K 31/506* (2013.01); *A61K 39/00* (2013.01); *A61K 45/06* (2013.01)

(58) Field of Classification Search
None
See application file for complete search history.

(56) References Cited

U.S. PATENT DOCUMENTS 8,410,153 B2 * 4/2013 Lahm et al. .................. 514/378

FOREIGN PATENT DOCUMENTS

| WO | 2007079162 | 7/2007 |
| WO | 2008154528 | 12/2008 |
| WO | 2009002809 | 12/2008 |
| WO | 2009045999 | 4/2009 |
| WO | 2010003923 | 1/2010 |
| WO | 2010079077 | 7/2010 |

* cited by examiner

*Primary Examiner* — Kamal Saeed
(74) *Attorney, Agent, or Firm* — Ann R. Pokalsky; Dilworth & Barrese, LLP

(57) ABSTRACT

The present invention relates to the use of compounds of formula

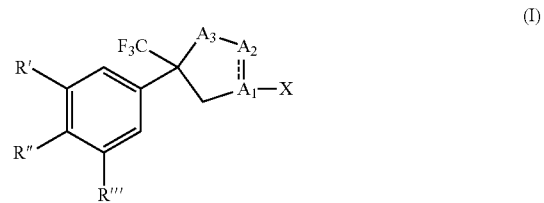

(I)

wherein the variables are as defined in the description, in the free form or in salt form, for controlling sea lice on fish.

10 Claims, No Drawings

USE OF SUBSTITUTED HETEROCYCLIC COMPOUNDS TO CONTROL SEA LICE ON FISH

This application is a 371 application of PCT/EP2011/059898, filed Jun. 15, 2011, the contents of which are incorporated by reference herein.

The present invention relates to the use of a compound of formula

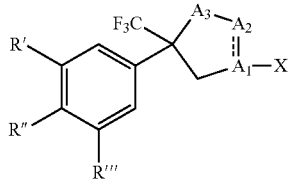

(I)

including all geometric and stereoisomers, N-oxides, S-oxides and salts thereof, wherein, R', R" and R'" are each independently hydrogen, halogen, cyano, $C_1$-$C_2$-alkyl, halo-$C_1$-$C_2$-alkyl, $C_1$-$C_2$-alkoxy or $C_1$-$C_2$-haloalkoxy, subject to the proviso that at least one of R', R" and R'" is not hydrogen;

$A_1$ is C, $A_2$ is N, $A_3$ is O, $CH_2$ or $NR_1'$ and the bond between $A_1$ and $A_2$ is a double bond; or $A_1$ is N, $A_2$ and $A_3$ are each $CH_2$ and the bond between $A_1$ and $A_2$ is a single bond;

$R_1'$ independently is as defined as $R_1$ below; and X is (a) a radical of formula

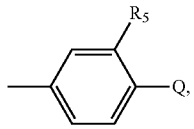

(II)

wherein $R_5$ is H, $C_1$-$C_2$-alkyl, $C_1$-$C_2$-haloalkyl, halogen, nitro or cyano and Q is (i) a 5- or 6-membered heteroaromatic ring comprising 1 to 3 same or different heteroatoms selected from the group consisting of O, S and N; or is (ii) a group —C(O)N($R_1$)-T, wherein $R_1$ is H, $C_1$-$C_4$-alkyl, $C_2$-$C_4$-alkylcarbonyl or $C_2$-$C_4$-alkoxycarbonyl and T is $C_1$-$C_6$-alkyl which is unsubstituted or substituted by $C_3$-$C_6$-cycloalkyl, halogen, cyano, nitro, amino, hydroxy, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulfinyl, $C_1$-$C_6$-haloalkylsulfinyl, $C_1$-$C_6$-alkylsulfonyl, $C_1$-$C_6$-haloalkylsulfonyl, carboxy, carbamoyl, $C_1$-$C_6$-alkylcarbonylamino, $C_1$-$C_6$-haloalkylcarbonylamino, $C_1$-$C_6$-alkoxycarbonyl, sulfonamido, N-mono- or N,N-di-$C_1$-$C_4$-alkylsulfonamido, $C_2$-$C_6$-alkanoyl, unsubstituted or in the alkyl portion by halogen, cyano, ethenyl or ethynyl substituted N—$C_1$-$C_6$-alkylaminocarbonyl, or unsubstituted or halogen-, $C_1$-$C_2$-alkyl-, $C_1$-$C_2$-haloalkyl or cyano-substituted 4- to 6-membered heterocyclyl; or T is $C_3$-$C_6$-cycloalkyl or 4- to 6-membered heterocyclyl, which is each unsubstituted or substituted by halogen, $C_1$-$C_2$-alkyl, $C_1$-$C_2$-haloalkyl or cyano; or is (iii) a radical —C(O)NH—C=N—O—$C_1$-$C_2$-alkyl, a radical —C(O)N=C—N-di-$C_1$-$C_2$-alkyl or a radical —C(O)N=C($NH_2$)—O—$C_1$-$C_2$-alkyl; or is (iv) a group —CH($R_3$)—N($R_4$)—C(O)-$T_1$, wherein $R_3$ is H, $C_1$-$C_6$-alkyl, $C_1$-$C_6$-haloalkyl, halogen or cyano, $R_4$ is H; $C_1$-$C_4$-alkyl $C_2$-$C_4$-alkylcarbonyl or $C_2$-$C_4$-alkoxycarbonyl, and $T_1$ is independently defined as T above;

(b) a radical of formula

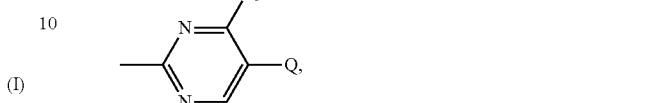

(III)

wherein $R_5'$ is H, $C_1$-$C_2$-alkyl, $C_1$-$C_2$-haloalkyl, halogen, nitro or cyano, and Q is as defined above;

(c) a radical of formula

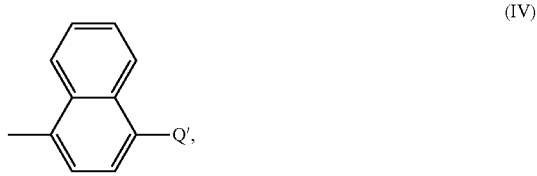

(IV)

wherein Q' is a radical as defined in embodiments (ii), (iii) and (iv) for Q above; or (d) a radical of formula

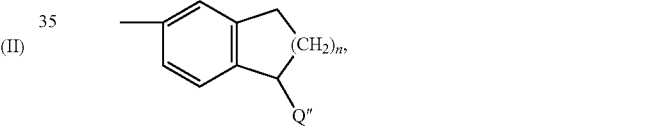

(V)

wherein n is 1 or 2 and Q" is a group —N($R_4$)—C(O)-$T_2$, wherein $T_2$ independently has the meaning of T above and $R_4$ is as defined above;

for controlling sea lice on fish.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers.

"Alkoxy" includes, for example, methoxy, ethoxy, n-propyloxy, isopropyloxy and the different butoxy, pentoxy and hexyloxy isomers. "Alkylthio" includes branched or straight-chain alkylthio moieties such as methylthio, ethylthio, and the different propylthio, butylthio, pentylthio and hexylthio isomers.

"Alkylsulfinyl" includes both enantiomers of an alkylsulfinyl group. Examples of "alkylsulfinyl" include $CH_3S(O)$—, $CH_3CH_2S(O)$—, $CH_3CH_2CH_2S(O)$—, $(CH_3)_2CHS(O)$— and the different butylsulfinyl, pentylsulfinyl and hexylsulfinyl isomers.

Examples of "alkylsulfonyl" include $CH_3S(O)_2$—, $CH_3CH_2S(O)_2$—, $CH_3CH_2CH_2S(O)_2$—, $(CH_3)_2CHS(O)_2$—, and the different butylsulfonyl, pentylsulfonyl and hexylsulfonyl isomers.

"N-alkylamino", "N,N-di-alkyamino", and the like, are defined analogously to the above examples.

"Cycloalkyl" includes, for example, cyclopropyl, cyclobutyl, cyclopentyl and cyclohexyl. The term "alkylcycloalkyl" denotes alkyl substitution on a cycloalkyl moiety and includes, for example, ethylcyclopropyl, i-propylcyclobutyl, 3-methylcyclopentyl and 4-methylcyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups.

The term "halogen", either alone or in compound words such as "haloalkyl", includes fluorine, chlorine, bromine or iodine. Further, when used in compound words such as "haloalkyl", said alkyl may be partially or fully substituted with halogen atoms which may be the same or different. Examples of "haloalkyl" include $F_3C-$, $ClCH_2-$, $CF_3CH_2-$ and $CF_3CCl_2-$. The terms "halocycloalkyl", "haloalkoxy", "haloalkylthio", and the like, are defined analogously to the term "haloalkyl". Examples of "haloalkoxy" include $CF_3O-$, $CCl_3CH_2O-$, $HCF_2CH_2CH_2O-$ and $CF_3CH_2O-$. Examples of "haloalkylthio" include $CCl_3S-$, $CF_3S-$, $CCl_3CH_2S-$ and $ClCH_2CH_2CH_2S-$. Examples of "haloalkylsulfinyl" include $CF_3S(O)-$, $CCl_3S(O)-$, $CF_3CH_2S(O)-$ and $CF_3CF_2S(O)-$. Examples of "haloalkylsulfonyl" include $CF_3S(O)_2-$, $CCl_3S(O)_2-$, $CF_3CH_2S(O)_2-$ and $CF_3CF_2S(O)_2-$.

"Alkylcarbonyl" denotes a straight-chain or branched alkyl moieties bonded to a $C(=O)$ moiety. Examples of "alkylcarbonyl" include $CH_3C(=O)-$, $CH_3CH_2CH_2C(=O)-$ and $(CH_3)_2CHC(=O)-$. Examples of "alkoxycarbonyl" include $CH_3OC(=O)-$, $CH_3CH_2OC(=O)$, $CH_3CH_2CH_2OC(=O)-$, $(CH_3)_2CHOC(=O)-$ and the different butoxy- or pentoxycarbonyl isomers, for example tert.-butoxycarbonyl (Boc).

The total number of carbon atoms in a substituent group is indicated by the "$C_i$-$C_j$" prefix where i and j are integers. For example, $C_1$-$C_4$ alkylsulfonyl designates methylsulfonyl through butylsulfonyl; $C_2$-alkoxyalkyl designates $CH_3OCH_2$; $C_3$-alkoxyalkyl designates, for example, $CH_3CH(OCH_3)$, $CH_3OCH_2CH_2$ or $CH_3CH_2OCH_2$; and $C_4$-alkoxyalkyl designates the various isomers of an alkyl group substituted with an alkoxy group containing a total of four carbon atoms, examples including $CH_3CH_2CH_2OCH_2$ and $CH_3CH_2OCH_2CH_2-$.

When a compound is substituted with a substituent bearing a subscript that indicates the number of said substituents can exceed 1, said substituents (when they exceed 1) are independently selected from the group of defined substituents, e.g., $(R_2)_n$, n is 1 or 2. "Aromatic" indicates that each of the ring atoms is essentially in the same plane and has aporbital perpendicular to the ring plane, and in which (4n+2) π electrons, where n is a positive integer, are associated with the ring to comply with Hückel's rule.

The terms "heterocyclic ring", "heterocycle" or "heterocyclyl" denote a ring in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. When a fully unsaturated heterocyclic ring satisfies Hückel's rule, then said ring is also called a "heteroaromatic ring", "aromatic heterocyclic ring". Unless otherwise indicated, heterocyclic rings and ring systems can be attached through any available carbon or nitrogen by replacement of a hydrogen on said carbon or nitrogen.

A 4- to 6-membered nitrogen-containing heterocyclic ring may be attached to the remainder of formula (I) though any available carbon or nitrogen ring atom, unless otherwise described.

R', R" and R'" are each independently of the other preferably H, halogen, $CF_3$ or cyano, and in particular H, Cl or F, subject to the proviso that at least one of R', R" and R'" is not H. One preferred embodiment of the invention concerns compounds of formula (I), wherein R' and R'" are each independently of the other chlorine or fluorine, in particular each chlorine, and R" is H.

One preferred embodiment of the invention relates to compounds of formula

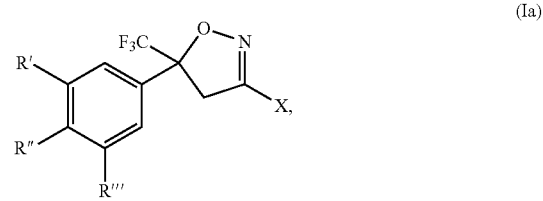

(Ia)

wherein for R, R', R" and X each the above and below given meanings and preferences apply.

A further preferred embodiment of the invention relates to compounds of formula

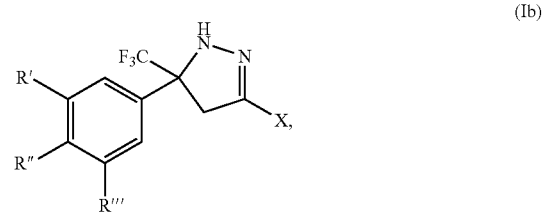

(Ib)

wherein for R, R', R" and X each the above and below given meanings and preferences apply.

A further preferred embodiment of the invention relates to compounds of formula

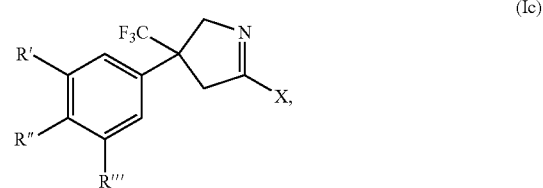

(Ic)

wherein for R, R', R" and X each the above and below given meanings and preferences apply.

Still a further preferred embodiment of the invention relates to compounds of formula

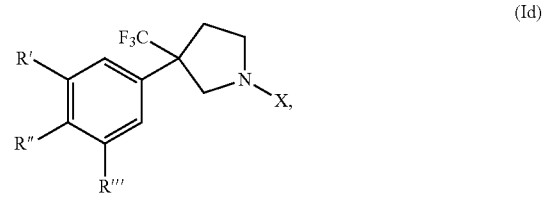

(Id)

wherein for R, R', R" and X each the above and below given meanings and preferences apply.

In formulae (I), (Ia), (Ib), (Ic) and (Id) above, X is, for example, a radical of formula (II); according to a further embodiment, X in formulae (I), (Ia), (Ib), (Ic) and (Id) above is a radical of formula (III), (IV) or (V), more preferably a radical of formula (IV) or (V), and in particular a radical of formula (IV).

The following preferences apply to the radicals of formulae (II) to (V):

$R_5$ is preferably H, methyl, chlorine, nitro, cyano or $CF_3$, and in particular methyl, chlorine $CF_3$ or cyano.

$R_5'$ is preferably H, $C_1$-$C_2$-alkyl, $C_1$-$C_2$-haloalkyl, halogen or cyano, preferably methyl, chlorine, or $CF_3$.

A suitable heterocyclic ring Q (embodiment (i)) is, for example, a 5- or 6-membered heteroaromatic ring having from 1 to 4, preferably from 1 to 3 same or different heteroatoms selected from the group consisting of N, O and S, which is further unsubstituted or substituted by one or more substituents selected from the group consisting of halogen, cyano, nitro, $C_1$-$C_4$-alkyl, $C_1$-$C_4$-haloalkyl, hydroxy, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, —COOH, —CONH$_2$, $C_1$-$C_4$-alkoxycarbonyl, sulfonamido, $C_2$-$C_3$-alkanoyl. The heteroaromatic ring Q is preferably unsubstituted or substituted by 1 to 3, in particular 1 or 2, same or different substituents selected from the group consisting of halogen, cyano, nitro, $C_1$-$C_2$-alkyl, $C_1$-$C_2$-haloalkyl, $C_1$-$C_2$-alkoxy, $C_1$-$C_2$-haloalkoxy, $C_1$-$C_2$-haloalkylthio, $C_1$-$C_4$-alkoxycarbonyl, $C_2$-$C_3$-alkanoyl.

Examples of a 5- or 6-membered heteroaromatic rings optionally substituted with from one or more substituents include the rings Q-1 through Q-60 illustrated in Exhibit 1 wherein R is any substituent as defined before including the preferences given, and r is an integer from 0 to 4, limited by the number of available positions on each Q group. As Q-28, Q-29, Q-35, Q-36, Q-37, Q-38, Q-39, Q-40, Q-41 and Q-42 have only one available position, for these Q groups r is limited to the integers 0 or 1, and r being 0 means that the Q group is unsubstituted and a hydrogen is present at the position indicated by $(R)_r$.

Exhibit 1

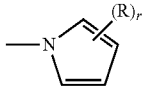
Q-1

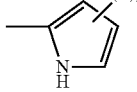
Q-2

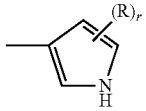
Q-3

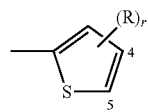
Q-4

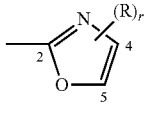
Q-5

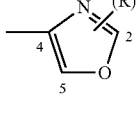
Q-6

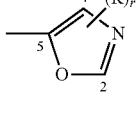
Q-7

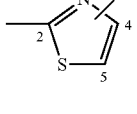
Q-8

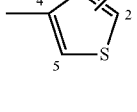
Q-9

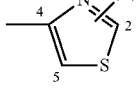
Q-10

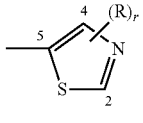
Q-11

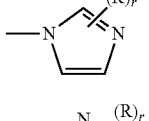
Q-12

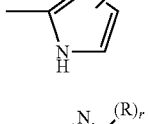
Q-13

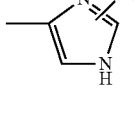
Q-14

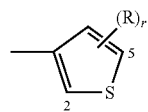
Q-15

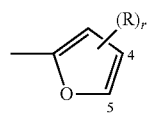
Q-16

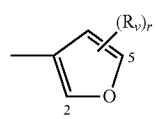
Q-17

Q-18 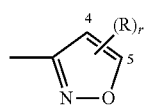
Q-19 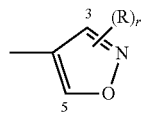
Q-20 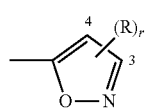
Q-21 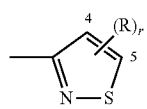
Q-22 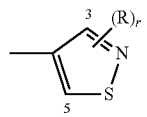
Q-23 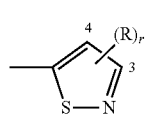
Q-24 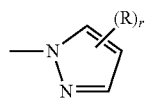
Q-25 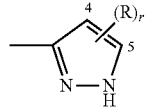
Q-26 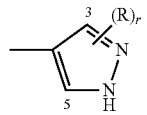
Q-27 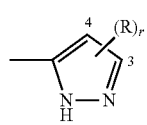
Q-28 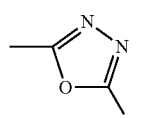
Q-29 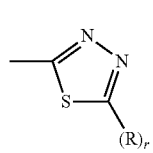
Q-30 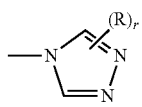
Q-31 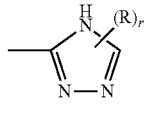
Q-32 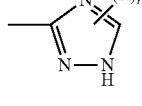
Q-33 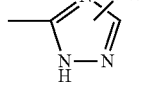
Q-34 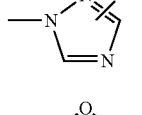
Q-35 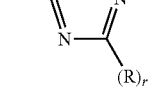
Q-36 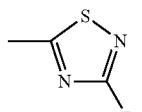
Q-36 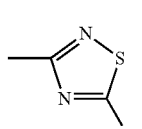
Q-38 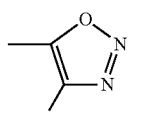
Q-39 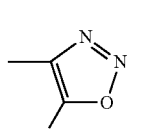
Q-40 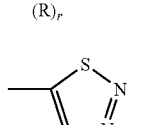
Q-41

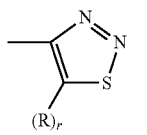
Q-42
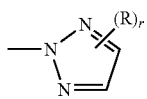
Q-43
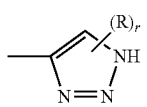
Q-44
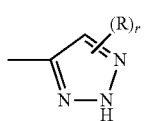
Q-45
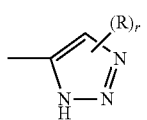
Q-46
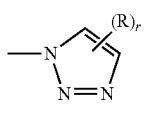
Q-47
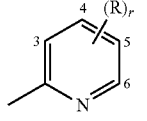
Q-48
Q-49
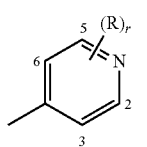
Q-50
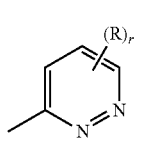
Q-51
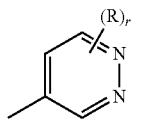
Q-52
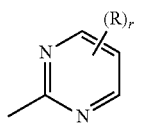
Q-53
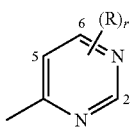
Q-54
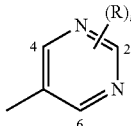
Q-55
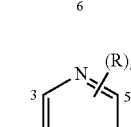
Q-56
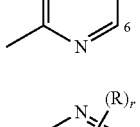
Q-57
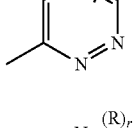
Q-58
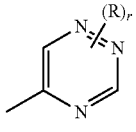
Q-58
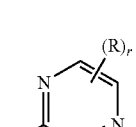
Q-60
A preferred heterocyclic ring Q is of formula
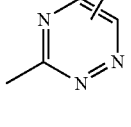
Q-5
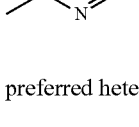
Q-6
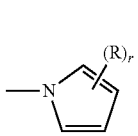
Q-7
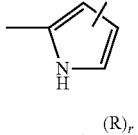
Q-14
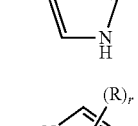

-continued

Q-15 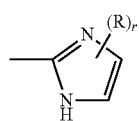

Q-16 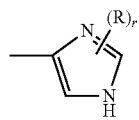

Q-17 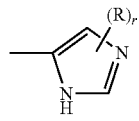

Q-24 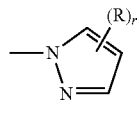

Q-26 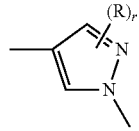

Q-30 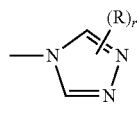

Q-31 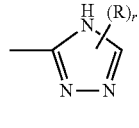

Q-32 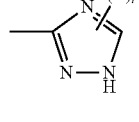

Q-33 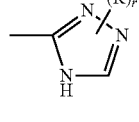

Q-34 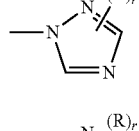

Q-43 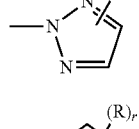

Q-47 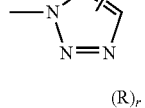

Q-49 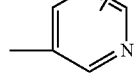

-continued

Q-50

Q-52

Q-54 wherein r is an integer from 0 to 3 and R is independently selected from the group given before for the heteroaromatic ring including the preferences. Q is particularly preferred the unsubstituted radical Q-14, Q-24, Q-34, Q-43 or Q-47, wherein r is 0 in each case. Q is especially preferred a radical Q-14, Q-34 or Q-47, wherein r is 0.

If Q is a group —C(O)N($R_1$)-T (embodiment (II)), $R_1$ is preferably H, methyl, ethyl or acetyl and in particular H.

T as alkyl is preferably $C_1$-$C_4$-alkyl, more preferably $C_1$-$C_2$-alkyl and particularly preferably $C_1$-alkyl, which is each unsubstituted or substituted as defined above.

The alkyl radical T is preferably unsubstituted or substituted by halogen, $C_1$-$C_4$-alkoxycarbonyl, unsubstituted or in the alkyl portion by halogen, cyano, ethenyl or ethynyl substituted N—$C_1$-$C_6$-alkylaminocarbonyl or unsubstituted or halogen-, $C_1$-$C_2$-alkyl- or $C_1$-$C_2$-haloalkyl-substituted 5- to 6-membered heterocyclyl; or is 4- to 6-membered heterocyclyl, which is each unsubstituted or substituted by halogen, $C_1$-$C_2$-alkyl or $C_1$-$C_2$-haloalkyl.

A preferred N-alkylaminocarbonyl substituent of the alkyl radical T is N—$C_1$-$C_2$-alkylaminocarbonyl, which is unsubstituted or further substituted in the alkyl moiety by halogen, cyano, ethenyl or ethynyl. Especially preferred N-alkylaminocarbonyl substituents of the alkyl radical T are N-ethylaminocarbonyl or a radical —C(O)NH—$CH_2CF_3$, —C(O)NH—$CH_2CN$, —C(O)NH—$CH_2CH$=$CH_2$ or —C(O)NH—$CH_2C$≡CH.

T as N-alkylaminocarbonyl-substituted alkyl is preferably N-ethylaminocarbonylmethyl, or a radical —$CH_2$—C(O)NH—$CH_2CF_3$, —$CH_2$—C(O)NH—$CH_2CN$ or —$CH_2$—C(O)NH—$CH_2C$≡CH.

If T is heterocyclyl-substituted alkyl, preferred meanings of heterocyclyl include pyridyl, pyrimidinyl, thiazolyl, oxazolyl or tetrahydrofuranyl. Preferred heterocyclyl-substituted alkyl radicals T are in particular 2-pyridylmethyl or 2-tetrahydrofuranylmethyl.

If T is 4- to 6-membered heterocyclyl, preferred meanings of heterocyclyl include pyridyl, pyrimidyl, thiazolyl, oxazolyl, tetrahydrofuranyl, thietanyl or oxetanyl and in particular 2-3- or 4-pyridyl, 3-4- or 5-pyrimidyl, 2- or 3-tetrahydrofuranyl, thietan-3-yl or oxetan-3-yl and even more preferred 5-Cl-pyrimid-3-yl, 3-tetrahydrofuranyl, thietan-3-yl or oxetan-3-yl.

If Q is a group —C(O)N($R_1$)-T, $R_1$ is preferably H, methyl, ethyl or acetyl and T is $C_1$-$C_2$-alkyl; $C_1$-$C_2$-haloalkyl; $C_1$-$C_2$-alkoxycarbonyl-$C_1$-$C_2$-alkyl; $C_1$-$C_2$-alkyl which is substituted by pyridyl, pyrimidinyl, thiazolyl, oxazolyl or tetrahydrofuranyl; $C_1$-$C_2$-alkyl which is substituted by unsubstituted or in the alkyl moiety by halogen, cyano, ethenyl or ethynyl substituted N—$C_1$-$C_2$-alkylaminocarbonyl; pyridyl; pyrimidyl; thiazolyl; oxazolyl; tetrahydrofuranyl; thietanyl; or oxetanyl.

If Q is a group —C(O)N($R_1$)-T, $R_1$ is most preferably H, methyl or ethyl, and T is $C_1$-$C_2$-alkyl; $C_1$-$C_2$-haloalkyl; methyl which is substituted by pyridyl, pyrimidinyl, thiazolyl, oxazolyl or tetrahydrofuranyl; methyl which is substituted by N—$C_1$-$C_2$-alkylaminocarbonyl or by N—$C_1$-$C_2$-alkylaminocarbonyl substituted in the alkyl moiety by halogen, cyano, ethenyl or ethynyl; pyridyl; pyrimidyl; tetrahydrofuranyl; thietanyl; or oxetanyl.

If Q is a group —C(O)N($R_1$)-T, $R_1$ is particularly preferably H, and T is $C_1$-$C_2$-alkyl; a radical —$CH_2CF_3$, N-ethylaminocarbonylmethyl; a radical —$CH_2$—C(O)NH—$CH_2CF_3$, —$CH_2$—C(O)NH—$CH_2CN$ or —$CH_2$—C(O)NH—$CH_2C\equiv CH$; 2-pyridylmethyl; 5-Cl-pyrimid-3-yl; 3-tetrahydrofuranyl; thietan-3-yl; or oxetan-3-yl.

Preferred radicals Q of embodiment (iii) are a radical —C(O)NH—C=N—O—$CH_3$, a radical —C(O)N=C—N-di-$CH_3$ or a radical —C(O)N=C($NH_2$)—O—$CH_3$.

If Q is a group —CH($R_3$)—N($R_4$)—C(O)-$T_1$ (embodiment (iv)), $R_3$ is preferably H or $C_1$-$C_2$-alkyl or cyano, more preferably H or methyl, and in particular H. $R_4$ is preferably H or $C_1$-$C_2$-alkyl, in particular H.

$R_4$ is preferably H or $C_1$-$C_2$-alkyl, in particular H.

$T_1$ as optionally substituted alkyl is preferably straight-chain or branched $C_1$-$C_4$-alkyl, which is each unsubstituted or substituted by $C_3$-$C_6$-cycloalkyl, halogen, cyano, $C_1$-$C_4$-alkoxy, $C_1$-$C_2$-haloalkoxy, $C_1$-$C_4$-alkylthio, $C_1$-$C_2$-haloalkylthio, $C_1$-$C_4$-alkylsulfinyl, $C_1$-$C_4$-haloalkylsulfinyl, $C_1$-$C_4$-alkylsulfonyl, $C_1$-$C_4$-haloalkylsulfonyl, $C_1$-$C_2$-alkylcarbonylamino, $C_1$-$C_2$-haloalkylcarbonylamino or 4- to 6-membered heterocyclyl. Especially preferred alkyl radicals $T_1$ are straight-chain or branched $C_1$-$C_4$-alkyl or $C_1$-$C_4$-alkyl which is substituted by cyclopropyl, halogen, cyano, $C_1$-$C_2$-alkoxy, $C_1$-$C_2$-alkylthio, $C_1$-$C_2$-alkylsulfinyl, $C_1$-$C_2$-alkylsulfonyl or $C_1$-$C_2$-haloalkylcarbonylamino, pyridyl, pyrimidyl, thiazolyl, oxazolyl, tetrahydrofuranyl, thietanyl, oxetanyl.

$T_1$ as alkyl is especially preferred straight-chain or branched $C_1$-$C_4$-alkyl, $C_1$-$C_3$-haloalkyl, cyclopropylmethyl, cyano-$C_1$-$C_2$-alkyl, $C_1$-$C_2$-alkoxy-$C_1$-$C_2$-alkyl, $C_1$-$C_2$-alkylthio-$C_1$-$C_2$-alkyl, $C_1$-$C_2$-alkylsulfinyl-$C_1$-$C_2$-alkyl or $C_1$-$C_2$-alkylsulfonyl-$C_1$-$C_2$-alkyl, in particular methyl or ethyl.

Particularly preferred alkyl radicals $T_1$ are straight-chain or branched $C_1$-$C_4$-alkyl or $C_1$-$C_2$-alkyl which is substituted by halogen, cyano, $C_1$-$C_2$-alkoxy, $C_1$-$C_2$-alkylthio or $C_1$-$C_2$-alkylsulfonyl.

If $T_1$ is $C_3$-$C_6$-cycloalkyl, said cycloalkyl is preferably cyclopropyl, cyclobutyl, cyclopentyl or cyclohexyl, in particular cyclopropyl.

If $T_1$ is 4- to 6-membered heterocyclyl, said heterocyclyl is preferably a thienyl, furyl, oxazolyl, thiazolyl, pyridyl or pyrimidinyl radical which is unsubstituted or substituted by $C_1$-$C_2$-alkyl, $C_1$-$C_2$-haloalkyl or $C_1$-$C_4$-alkoxycarbonyl. Especially preferred heteroaromatic radicals $T_1$ are 2-, 3- or 4-pyridyl, 2- or 4-pyrimidinyl, 2-thiazolyl, 2-furyl or 2-thienyl.

A further preferred heterocyclic radical $T_1$ is, for example, a 4- to 6-membered heteroaliphatic ring selected from the group of thietanyl, for example thietan-3-yl, oxo-thietanyl, dioxo-thietanyl, oxetanyl, for example oxetan-3-yl, azetidinyl, pyrrolidinyl, tetrahydrofuranyl, tetrahydrothiophenyl, piperidinyl, piperazinyl, morpholinyl, tetrahydropyranyl and thianyl which are each unsubstituted or substituted by $C_1$-$C_2$-alkyl, $C_1$-$C_2$-haloalkyl or $C_1$-$C_4$-alkoxycarbonyl. Especially preferred heteroaliphatic ring radicals $T_1$ include pyrrolidinyl, tetrahydrofuranyl, tetrahydrothiophenyl, piperidinyl, piperazinyl, morpholinyl or thianyl which are each unsubstituted or substituted by $C_1$-$C_2$-alkyl, $C_1$-$C_2$-haloalkyl or $C_1$-$C_4$-alkoxycarbonyl, and in particular pyrrolidine-1-yl, tetrahydrofuran-2-yl, piperidine-1-yl, morpholine-4-yl or thiane-4-yl.

Q as a group —CH($R_3$)—N($R_4$)—C(O)-$T_1$ is most preferably a radical —$CH_2$—NH—C(O)—$C_1$-$C_2$-alkyl, —$CH_2$—NH—C(O)-cyclopropyl, —$CH_2$—NH—C(O)—($CH_2$)$_{1-2}$—O—$C_1$-$C_2$-alkyl, —$CH_2$—NH—C(O)—($CH_2$)$_{1-2}$—S—$C_1$-$C_2$-alkyl or —$CH_2$—NH—C(O)—($CH_2$)$_{1-2}$—S(O)$_2$—$C_1$-$C_2$-alkyl.

Particular preferred meanings of Q are a radical (q1)
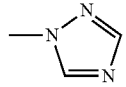

(q2)
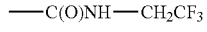

(q3)
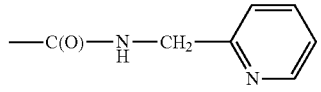

(q4)
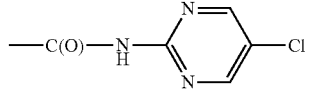

(q5)
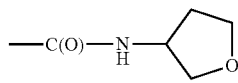

(q6)
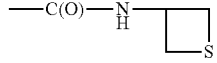

(q7)
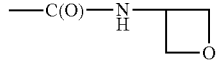

(q8) —C(O)NH—$CH_2$—C(O)NH—$CH_2CF_3$
(q9) —C(O)NH—$CH_2$—C(O)NH—$CH_2CN$
(q10) —C(O)NH—$CH_2$—C(O)NH—$CH_2C\equiv CH$
(q11) —C(O)NH—C=N—O—$CH_3$
(q12) —C(O)N=C—N($CH_3$)$_2$
(q13) —C(O)N=C($NH_2$)—O—$CH_3$
(q14) —$CH_2$—NH—C(O)—$C_1$-$C_3$-alkyl
(q15) —$CH_2$—NH—C(O)-cyclopropyl
(q16) —$CH_2$—NH—C(O)—$C_1$-$C_2$-haloalkyl
(q17) —$CH_2$—NH—C(O)—$CH_2$—S—$C_1$-$C_2$-alkyl
(q18) —$CH_2$—NH—C(O)—$CH_2$—S(O)$_2$—$C_1$-$C_2$-alkyl
(q19) —$CH_2$—NH—C(O)—($CH_2$)$_{1-2}$—O—$C_1$-$C_2$-alkyl.

For Q' all the meanings and preferences given above for embodiments (ii), (iii) and (iv) of Q independently apply. Particularly preferred radicals Q' are the radicals (q2)-(q19) as mentioned above.

If Q" is a group —N($R_4$)—C(O)-$T_2$, for $R_4$ each the above given meanings and preferences apply independently; in addition, for $T_2$ each the meanings and preferences given above for T apply. Particular preferred meanings of Q" are a radical (q20) —NH—C(O)—$C_1$-$C_3$-alkyl,
(q21) —NH—C(O)-cyclopropyl,
(q22) —NH—C(O)—$C_1$-$C_2$-haloalkyl,
(q23) —NH—C(O)—$CH_2$—S—$C_1$-$C_2$-alkyl,
(q24) —NH—C(O)—$CH_2$—$S(O)_2$—$C_1$-$C_2$-alkyl or
(q25) —NH—C(O)—$(CH_2)_{1-2}$—O—$C_1$-$C_2$-alkyl.

A group of preferred compounds for use in the control of sea lice are those of formula

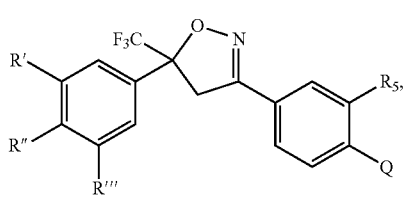
(Ia')

wherein R', R" and R'" are each independently of the other H, halogen or trifluoromethyl, subject to the proviso, that at least one of R', R" and R'" is not H, $R_5$ is methyl, chlorine $CF_3$ or cyano and Q is (i) a radical Q-14, Q-24, Q-34, Q-43 or Q-47 mentioned above, wherein r is 0 in each case;

(ii) a radical —C(O)N($R_1$)-T, wherein $R_1$ is H, methyl, ethyl or acetyl, and T is $C_1$-$C_2$-alkyl; $C_1$-$C_2$-haloalkyl; $C_1$-$C_2$-alkoxycarbonyl-$C_1$-$C_2$-alkyl; $C_1$-$C_2$-alkyl which is substituted by pyridyl, pyrimidinyl, thiazolyl, oxazolyl or tetrahydrofuranyl; $C_1$-$C_2$-alkyl which is substituted by unsubstituted or in the alkyl moiety by halogen, cyano, ethenyl or ethynyl substituted N—$C_1$-$C_2$-alkylaminocarbonyl; pyridyl; pyrimidyl; thiazolyl; oxazolyl; tetrahydrofuranyl; thietanyl; or oxetanyl;

(iii) a radical —C(O)NH—C=N—O—$CH_3$, —C(O)N=C—N-di-$CH_3$ or —C(O)N=C($NH_2$)—O—$CH_3$; or (iv) a radical —CH($R_3$)—N($R_4$)—C(O)-$T_1$ wherein $R_3$ is H, $C_1$-$C_2$-alkyl or cyano, $R_4$ is H or $C_1$-$C_2$-alkyl, and $T_1$ is straight-chain or branched $C_1$-$C_4$-alkyl, $C_1$-$C_3$-haloalkyl, cyclopropylmethyl, cyano-$C_1$-$C_2$-alkyl, $C_1$-$C_2$-alkoxy-$C_1$-$C_2$-alkyl, $C_1$-$C_2$-alkylthio-$C_1$-$C_2$-alkyl, $C_1$-$C_2$-alkylsulfinyl-$C_1$-$C_2$-alkyl or $C_1$-$C_2$-alkylsulfonyl-$C_1$-$C_2$-alkyl, cyclopropyl, unsubstituted or $C_1$-$C_2$-alkyl-, $C_1$-$C_2$-haloalkyl- or $C_1$-$C_4$-alkoxycarbonyl-substituted thienyl, furyl, oxazolyl, thiazolyl, pyridyl or pyrimidinyl.

A group of particularly preferred compounds for use in the control of sea lice are those of formula (Ia') above, wherein R' and R'" are each independently of the other chlorine or fluorine, R" is H, $R_5$ is methyl or cyano and Q is a radical (q1) to (q19) as mentioned above.

A further group of preferred compounds for use in the control of sea lice are those of formula

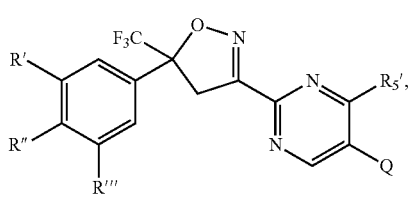
(Ia")

wherein R', R" and R'" are each independently of the other H, halogen or trifluoromethyl, subject to the proviso, that at least one of R', R" and R'" is not H, $R_5$' is methyl, halogen, $CF_3$ or cyano, and for Q independently the meanings and preferences given above apply.

A further group of preferred compounds for use in the control of sea lice are those of formula

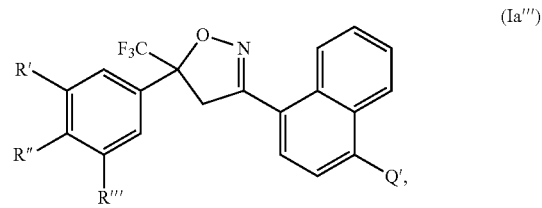
(Ia''')

wherein R', R" and R'" are each independently of the other H, halogen or trifluoromethyl, subject to the proviso, that at least one of R', R" and R'" is not H, and Q' is (ii) a group —C(O)N($R_1$)-T, wherein $R_1$ is H, methyl, ethyl or acetyl, and T is $C_1$-$C_2$-alkyl; $C_1$-$C_2$-haloalkyl; $C_1$-$C_2$-alkoxycarbonyl-$C_1$-$C_2$-alkyl; $C_1$-$C_2$-alkyl which is substituted by pyridyl, pyrimidinyl, thiazolyl, oxazolyl or tetrahydrofuranyl; $C_1$-$C_2$-alkyl which is substituted by unsubstituted or in the alkyl moiety by halogen, cyano, ethenyl or ethynyl substituted N—$C_1$-$C_2$-alkylaminocarbonyl; pyridyl; pyrimidyl; thiazolyl; oxazolyl; tetrahydrofuranyl; thietanyl; or oxetanyl;

(iii) a radical —C(O)NH—C=N—O—$CH_3$, —C(O)N=C—N-di-$CH_3$ or —C(O)N=C($NH_2$)—O—$CH_3$; or (iv) a group —CH($R_3$)—N($R_4$)—C(O)-$T_1$ wherein $R_3$ is H, $C_1$-$C_2$-alkyl or cyano, $R_4$ is H or $C_1$-$C_2$-alkyl, and $T_1$ is straight-chain or branched $C_1$-$C_4$-alkyl, $C_1$-$C_3$-haloalkyl, cyclopropylmethyl, cyano-$C_1$-$C_2$-alkyl, $C_1$-$C_2$-alkoxy-$C_1$-$C_2$-alkyl, $C_1$-$C_2$-alkylthio-$C_1$-$C_2$-alkyl, $C_1$-$C_2$-alkylsulfinyl-$C_1$-$C_2$-alkyl or $C_1$-$C_2$-alkylsulfonyl-$C_1$-$C_2$-alkyl, cyclopropyl, unsubstituted or $C_1$-$C_2$-alkyl-, $C_1$-$C_2$-haloalkyl- or $C_1$-$C_4$-alkoxycarbonyl-substituted thienyl, furyl, oxazolyl, thiazolyl, pyridyl or pyrimidinyl.

A particularly preferred embodiment of the invention relates to compounds of the formula (Ia") above wherein R' and R'" are each independently of the other chlorine or fluorine, R" is H, and Q is a radical (q2) to (q19) as mentioned above.

Still a further group of preferred compounds for use in the control of sea lice are those of formula

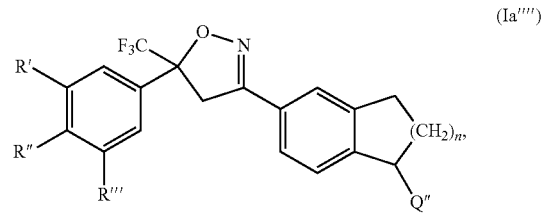
(Ia'''')

wherein R', R" and R'" are each independently of the other H, halogen or trifluoromethyl, subject to the proviso, that at least one of R', R" and R'" is not H, n=1 or 2, and for Q" each the above given meanings and preferences apply.

The compound of the formula I is used either alone or in combination with either another compound known to be active against sea lice, or a vaccine component including immune enhancing agents.

Suitable compounds known to be active against sea lice are, for example, hydrogen peroxide, formaldehyde, trichlorfon, malathion dichlorvos, azamethiphos, ivermectin, emamectin benzoate, moxidectin, teflubenzuron diflubenzuron, hexaflumuron, lufenuron, fluazuron, cypermethrin cis-40:trans-60, deltamethrin, high cis cypermethrin cis-80:trans-20, imidacloprid, nitenpyram, thiamethoxam, thiacloprid, clothianidin, acetamiprid spinosad, epofenonane, triprene, methoprene, hydroprene, kinoprene, phenoxycarb.

Preferred combination partners are an organophosphate, a pyrethroid such as cypermethrin or deltamethrin, a macrocyclic lactone such as emamectin benzoate, hydrogen peroxide or a benzoylurea, such as diflubenzuron, lufenuron or hexaflumuron.

The invention also relates to a method of controlling sea lice as well as to the use of these compounds or enantiomers thereof for the preparation of corresponding antiparasitic compositions.

The compounds of formula I are known from literature, for example from, WO 2005/085216, WO 2007/026965, WO 2007/070606, WO 2007/075459, WO 2007/079162, WO 2007/108448, WO 2007/123855, WO 2008/019760, WO 2009/022746, WO 2009/035004, WO 2009/080250 or WO 2009/112275, primarily for pest control in the field of crop protection.

The compounds of formula I may be present in the form of enantiomers. The preparation and isolation of enantiomers is known per se. Accordingly, any reference to compounds of formula I hereinbefore and hereinafter is understood to include also their pure enantiomeric forms, even if the latter are not specifically mentioned in each case.

The compounds of formula I can form salts, for example acid addition salts. These are formed for example with strong inorganic acids, typically mineral acids, e.g. sulfuric acid, a phosphoric acid or a halogen acid, or with strong organic carbonic acids, typically $C_1$-$C_4$-alkanecarbonic acids substituted where appropriate for example by halogen, e.g. acetic acid, such as dicarbonic acids that are unsaturated where necessary, e.g. oxalic, malonic, maleic, fumaric or phthalic acid, typically hydroxycarbonic acids, e.g. ascorbic, lactic, malic, tartaric or citric acid, or benzoic acid, or with organic sulfonic acids, typically $C_1$-$C_4$-alkane or arylsulfonic acids substituted where appropriate for example by halogen, e.g. methanesulfonic or p-toluenesulfonic acid. In a broader sense, compounds of formula I with at least one acid group can form salts with bases. Suitable salts with bases are for example metal salts, typically alkali or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl, diethyl, triethyl or dimethylpropylamine, or a mono-, di- or trihydroxy-lower alkylamine, e.g. mono-, di- or triethanolamine. Furthermore, where appropriate corresponding internal salts may also be formed. The free form is preferred. Among the salts of compounds of formula I, the hydrochemically beneficial salts are preferred. Hereinbefore and hereinafter, the free compounds of formula I and their salts are understood where appropriate to include also by analogy the corresponding salts or free compounds of formula I. The same applies for the pure enantiomers of formula I and salts thereof.

Unless otherwise defined, the general terms used hereinabove and hereinbelow have the meanings given hereinbelow.

Intensive fish farming can sustain substantial economical losses through the injury of fish by sea lice. Treatments against these parasites are known; the conventional active substances, are used over a range of concentrations and require differing treatment periods. Some of these active substances therefore cannot fully meet the requirements of a low-dose treatment, which is why there is still a need for the provision of further compounds having properties for controlling fish-parasitic crustaceans, which object is achieved according to this invention by the use of compounds I.

In accordance with this invention the compounds of formula I are excellently suited for use in the control of fish-parasitic crustaceans. These include the Family Caligidae with representative genus *Dissonus*, *Caligus* (i.e. *C. curtus*, *C. elongatus*, *C. clemensi*, *C. rogercresseyii*), and *Lepeophtheirus* (i.e. *L. salmonis*); Families Cecropidae, Dichelesthiidae, Lernaeopodidae with representative genus *Salmincola;* Families Pandaridae, Pennellidae with representative genus *Lernaeocera* and *Pennella;* and Family Sphyriidae; Family Lernaeidae with representative genus *Lernaea;* Families Bomolochidae, Chondracanthidae, Ergasilidae and Philichthyidae.

The fish include food fish, breeding fish, aquarium, pond, river, reservoir fish of all ages occurring in freshwater, sea water and brackish water. For example, bass, bream, carp, catfish, char, chub, cichlid, cod, eel, flounder, gourami, grayling, grouper, halibut, mullet, plaice, pompano, roach, rudd, salmon, sole, tilapia, trout, whitefish, yellowtail.

The compositions of this invention are particularly suitable for treating salmon. The term "salmon" within the scope of this invention will be understood as comprising all representatives of the family Salmonidae, especially of the subfamily salmoninae, and preferably, the Atlantic salmon (*Salmon salar*), rainbow trout (*Oncorhynchus mykiss*), brown or sea trout (*S. trutta*), the Pacific salmon: Cherry salmon or seema (*O. masou*), Taiwanese salmon (*O. masou formosanum*), chinook salmon or King salmon (*O. tshawytscha*), chum salmon or Calico salmon (*O. keta*), coho salmon or silver salmon (*O. kisutch*), pink salmon (*O. gorbuscha*), Sockeye salmon or Red salmon (*O. nerka*), artifically propagated species, such as *Salmo clarkii*, and *Salvelinus* species such as Brook trout (*S. fontinalis*).

Preferred objects of the present invention are the Atlantic and Pacific salmon and the sea trout.

In present-day salmon and trout farming, juvenile fish are transferred in the smolt stage from fresh-water tanks or cages to sea water cages. These latter are cubic, rectangular or also round cages having a metal or plastic frame which is covered with a fairly fine-meshed net. These cages are lowered into the sea until they are 9/10 submerged and then so anchored that they are accessible from the top. Other cages can be positioned such that the fish in the cage are kept submerged by either placing a physical barrier, such as a mesh net within the cage below the water surface or by fitting an upper mesh on the cage and fully submerging the structure.

In another variant, the fish are kept in sea water tanks of different shape. The cages are moored in sea inlets such that a flow of water passes through them in order to ensure a sufficient supply of oxygen. A constant flow of salt water in the sea water tanks is also maintained along with a supply of oxygen. In this artificial environment the fish are fed and, if necessary, provided with medication to ensure welfare and health until they mature sufficiently for marketing as edible fish or are selected for further breeding.

Sustainable cage stocking is maintained in these fish farms. The fish density reaches 10 to 25 kg fish/$m^3$. The fish densities coupled with the other stress factors cause the caged fish to become in general more susceptible to disease, epidemics and parasites than their free-living co-specifics. In order to maintain healthy populations, the caged fish must be monitored and treated accordingly with vaccines and bactericides.

Besides infectious diseases, the prime threat in commercial salmon farming is, however, attack by the above-mentioned fish-parasitic crustaceans. In particular, two representatives of the class of Copepodae (cyclops) cause substantial losses in yield: *Lepeophtheirus* (*L. salmonis*) and *Caligus* (*C. elongatus* and *C. rogercresseyii*). These parasites are popularly known as sea lice. They are easily recognized: *Lepeophtheirus* has a brown, horseshoe-shaped carapace; *Caligus* is also brown, but much smaller. However, the intensity of pigmentation varies in both species.

These sea lice injure the fish by feeding on the scales, epithelium and the mucosa. When infestation is severe, these parasites also damage underlying dermis. As a consequence, secondary infections and osmotic imbalance will occur, even if the sea lice are removed. In extreme cases, severe wounding resulting from infestation by these parasites leads to further tissue damage caused by ultraviolet radiation or to the death of the fish from osmoregulatory failure or the secondary infections.

Sea lice are meanwhile widely prevalent and encountered in most fish farms. Severe infestation kills the fish. Mortality rates of over 50%, based on sea lice infestation, have been reported from Norwegian fish farms. The extent of the damage depends on the time of year and on environmental factors, for example the salinity of the water and average water temperature. In a first phase, sea lice infestation is seen in the appearance of the parasites attached to the fish and later—even more clearly—from the damage caused to skin and tissue. The most severe damage is observed in smolts which are just in the phase in which they have changed from fresh water to sea water and in broodstock fish which have stopped feeding. The situation is made even worse by the specific conditions in the fish farms, where salmon of different age groups but not necessarily of the same weight class are kept together; where fouled nets or cages are used; where high salt concentrations are to be found; where flow through the nets and cages is minimal and the fish are kept in a very narrow space.

Fish farmers who are confronted with this parasite problem usually suffer substantial financial losses and carry additional expenses. On the one hand, their fish are debilitated and damaged by the lice, resulting in lower rates of growth increase, and on the other hand, secondary infections have to be controlled with expensive drugs and labour-intensive measures. The fish can often no longer be sold, as the consumer will reject the damaged fish. This parasitic infestation can pose a threat to the salmon farmer's livelihood.

The worst damage is caused by *Lepeophtheirus*, as even few parasites cause widespread tissue damage. The life cycle of *Lepeophtheirus* consists substantially of three free-swimming larval stages (nauplius I & II and copepodid stages), the copepodids attach to the fish and develop through four chalimus stages, two pre-adult stages and the actual adult stage. The chalimus and adult stages are host-dependent.

The most dangerous stages, because they cause the greatest damage, are all those parasitizing on the fish, especially the adult stages.

Pest control agents which can be used to combat sea lice are commercially available, for example organophosphates, pyrethroids, emamectin benzoate, hydrogen peroxide or benzoylureas. Not all of these have always been available complicating resistance control programs. A shortcoming of some of these compounds can be the high concentrations in which they have to be used, the ecological problems associated therewith, and also increasing resistance. Surprisingly, in the compounds of formula I, substances have been found which, while having very low toxicity to fish, is even more effective and, in particular, whose photolytic and hydrolytic degradability is more rapid as compared with the known sea lice control agents and, furthermore, which can be successfully used against all chalimi, pre-adult and adult stages of sea lice on fish.

A further advantageous property of the compounds of formula I is that, at the proposed concentrations and anticipated low levels in the environment, other marine animals such as lobsters, oysters, crustaceans (with the exception of sea lice), fish and marine plants do not suffer injury. Its degradation products are in any case non-injurious to marine fauna and flora.

The fish is, for example, treated orally, e.g. via an in-feed treatment, wherein the compound of formula (I) is added to the feed provided to the fish.

According to a further embodiment, the fish is treated by bath treatment, wherein the compound of formula (I) is dissolved or suspended in the surrounding water of the fish and sea lice. For example, the fish are placed in a "medicinal bath" where they are kept for a period of time (minutes to several hours) e.g. when being transferred from one breeding basin to another.

According to a further embodiment, treatment can also be carried out parenterally; for example, the treatment comprises administration of the compound of formula (I) as injectable, wherein a liquid formulation of the active substance is injected into the fish.

It is also possible to treat the biotope of the fish temporarily or continuously with a compound of formula (I), e.g the net cages, entire ponds, aquaria, tanks or basins in which the fish are kept.

The active substance is administered in formulations which are adjusted to the applications. Formulations for oral administration are, for example, powders, premixes, granulates, solutions, emulsions, micro/nanoemulsions, emulsifiable concentrates, suspensions, nanosuspensions or suspension concentrates which are mixed homogeneously as feed additives with the feed, or powders, premixes, granulates, solutions, emulsions, micro/nanoemulsions, emulsifiable concentrates, suspensions, nanosuspensions or suspension concentrates which are administered in the form of pills, the outer coat of which can consist e.g. of fish feed compositions which cover the active substance completely. Formulations for bath application or for treating the biotope are powders, granulates, solutions, emulsions, micro/nanoemulsions, emulsifiable concentrates, suspensions, nanosuspensions, or suspension concentrates, tablets or the active substance itself. The user may use these formulations in diluted or undiluted form.

The active substance in these formulations is used, for example, in pure form, as a solid active substance e.g. in a specific particle size and/or polymorphic form or, preferably, together with—at least—one of the adjuvants which are conventionally used in formulation technology, such as extenders, typically solvents or solid carriers, or surface-active compounds (surfactants).

The formulations are prepared in a manner known per se, typically by mixing, granulating and/or compacting the active substance with solid or liquid carriers, where appropriate with the addition of further adjuvants, such as emulsifiable or dispersing agents, solubilisers, colourants, antioxidants and/or preservatives.

In practice it is also possible to use, for example, those forms of application where the active substance is contained in a readily water-soluble matrix of a film, or in films from which it diffuses over the period of application.

The active substance itself, in ground form or in one of the above formulations, can be used in water-soluble packagings, e.g. in polyvinyl alcohol bags which can be used together with the closed packaging. In this case the user in no longer exposed to the active substance or its formulation.

It is also possible to use semi-solid formulations for the bath treatment. The active substance, which is suspended or dissolved in oily or fatty matrices, is washed out. The release can be controlled by the choice of adjuvants, concentration of the active substance and form (surface). Coprimates or melts of hard fats comprising the active substance are also suitable for use.

The diluted compositions of this invention are prepared by contacting the active substance of formula I with liquid and/or solid formulation assistants by stepwise mixing and/or grinding such that an optimal development of the activity against sea lice of the formulation is achieved which conforms with the application.

The formulation steps can be supplemented by kneading, granulating (granulates) and, if desired, compressing (pills, tablets).

Formulation assistants can be, for example, solid carriers, solvents and, where appropriate, surface-active substances (surfactants) which are non-toxic for marine fauna and flora. The following formulation assistants can be typically used for preparing the compositions of this invention:

Solid carriers are, for example, kaolin, talcum, bentonite, sodium chloride, calcium phosphate, carbohydrates, lactose, sucrose, mannitol, sorbitol, starch, powdered cellulose, microcrystalline cellulose, cotton seed meal, polyethylene glycol ether, if necessary binders such as gelatin, soluble cellulose derivatives, pregelatinized starch, if desired with the addition of surface-active compounds such as ionic or non-ionic dispersants; also natural mineral fillers such as calcite, montmorillonite or attapulgite. To improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pre-granulated materials of inorganic or organic nature can be used, e.g. especially dolomite or pulverized plant residues. The active substance can also be added to sorptive organic materials, such as polyacrylates, and be applied in this form.

Suitable solvents are: aromatic hydrocarbons which may be partially hydrogenated, preferably the fractions containing 8 to 12 carbon atoms, e.g. alkylbenzenes or xylene mixtures, alkylated napthalenes or tetrahydronaphthalenes, aliphatic or cycloaliphatic hydrocarbons such as paraffins or cyclohexane, alkyl esters such as ethyl acetate or butyl acetate, alcohols such as ethanol, isopropanol, propanol, butanol or benzyl alcohol, polyethlyleneglycols such as PEG 200, PEG 300, PEG 400 or methoxy-polyethyleneglycol, tetraglycol, glycofurol, glycerol formal, dimethyl isosorbide, propylene carbonate, γ-hexalactone, ethyl lactate, benzyl benzoate, glycerol and its derivatives such as glycerol triacetate or glycerol triproprionate, isopropylidene glycerol, glycols and their ethers and esters, such as propylene glycol, diethylene glycol monoethyl ether, diethylene glycol diethyl ether, dipropylene glycol ether, dipropylene glycol monomethyl ether, ethylene glycol or ethylene glycol monomethyl ether or ethylene glycol monoethyl ether, ketones such as cyclohexanone, isophorone or diacetanol alcohol, strongly polar solvents such as N-methyl-2-pyrrolidone, 2-pyrrolidone, dimethyl sulfoxide, N,N-dimethyl acetamide or N,N-dimethyl formamide, water, as well as vegetable oils or epoxidized vegetable oils such as epoxidized rape-seed oil, castor oil, coconut oil or soybean oil, and silicone oils, isopropylmyristate, propylene glycol dicaprylate/dicaprate, medium chain triglycerides or ethyl oleate.

Depending of the type of formulation, suitable surface-active compounds are nonionic, cationic and/or anionic surfactants having good emulsifying, dispersing and wetting properties. The surfactants indicated hereinafter are only quoted as examples; the relevant literature describes many more surfactants which are conventionally used in formulation technology and which are suitable according to this invention.

Suitable nonionic surfactants are preferably polyglycol ether derivatives of aliphatic or cycloaliphatic alcohols, or saturated or unsaturated fatty acids, and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols. Further suitable nonionic surfactants are the water-soluble polyadducts of polyethylene oxide with polypropylene glycol, ethylenediaminopolypropylene glycol and alkylpolypropylene glycol containing 1 to 10 carbon atoms in the alkyl chain, which polyadducts contain 20 to 250 ethylene glycol ether groups and 10 to 100 propylene glycol ether groups. These compounds usually contain 1 to 5 ethylene glycol units per propylene glycol unit. Illustrative examples of nonionic surfactants are sorbitan fatty acid esters, polyoxyethylene sorbitan fatty acid esters, polyoxyethlylene alkyl ethers, polyoxyethylene alkyl ethers, polyglycerides, polyethylene glycol-15-hydroxystearate, nonylphenol polyethoxyethanols, polyethoxylated castor oil, polyadducts of polypropylene and polyethylene oxide, tributylphenoxy polyethoxyethanol, polyethylene glycol and octylphenoxy polyethoxyethanol. Fatty acid esters of polyoxyethylene sorbitan are also suitable nonionic surfactants, typically polyoxyethylene sorbitan tri-oleate.

Cationic surfactants are preferably quaternary ammonium salts carrying, as substituent, at least one $C_8$-$C_{22}$alkyl radical and, as further substituents, optionally halogenated lower alkyl, benzyl or hydroxy-lower alkyl radicals. The salts are preferably in the form of halides, methyl sulfates or ethyl sulfates, for example stearyl trimethylammonium chloride or benzyl bis(2-chloroethyl)ethyl ammonium bromide.

Suitable anionic surfactants may be water-soluble soaps as well as water-soluble synthetic surface-active compounds. Suitable soaps are the alkali metal salts, alkaline earth metal salts, ammonium salts or substituted ammonium salts of higher fatty acids ($C_{10}$-$C_{22}$), e.g. the sodium or potassium salts of oleic or stearic acid, or of natural fatty acid mixtures which can be obtained, inter alia, from coconut oil or tallow oil. Further suitable soaps are also the fatty acid methyl taurin salts. More often, however, so-called synthetic surfactants are used, especially fatty alcohol sulfonates, fatty alcohol sulfates, sulfonated benzimidazole derivatives or alkylarylsulfonates. The fatty alcohol sulfonates or sulfates are usually in the form of alkali metal salts, alkaline earth metal salts, ammonium salts or substituted ammonium salts, and they normally contain a $C_8$-$C_{22}$alkyl radical which also includes the alkyl moiety of acyl radicals, e.g. the sodium or calcium salt of ligninsulfonic acid, or dodecylsulfate, or of a mixture of fatty alcohol sulfates obtained from natural fatty acids. These compounds also comprise the salts of sulfated or sulfonated fatty alcohol/ethylene oxide adducts. The sulfonated benzimidazole derivatives preferably contain two sulfonic acid groups and one fatty acid radical containing 8 to 22 carbon atoms. Illustrative examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Corresponding phosphates, typically salts of the phosphoric acid ester of an adduct of p-nonylphenol with 4 to 14 mol of ethylene oxide, or phospholipids, are also suitable.

Suitable binders for water-soluble granulates or tablets are, for example, chemically modified polymeric natural substances which are soluble in water or in alcohol, such as starch, cellulose or protein derivatives (e.g. methyl cellulose, carboxymethyl cellulose, ethylhydroxyethyl cellulose, proteins such as gelatin and the like), as well as synthetic polymers, typically polyvinyl alcohol, polyvinyl pyrrolidone etc. Tablets may also contain, for example, fillers (e.g. starch, microcrystalline cellulose, sugar, lactose etc.), lubricants and disintegrators.

The bath application of the compositions of this invention to the sealice to be controlled can be carried out, for example, such that the compositions are placed in the cage in the form of solutions, emulsions, suspensions, powders or tablets, where they are quickly dissolved and/or dispersed by the movement of the fish and the flow of the water. Concentrated solutions can also be diluted with large volumes of water before being placed into the cages. Concentration problems do not normally occur in the cages because the fish, in expectation of food, move wildly whenever the cages are opened, thereby promoting fast dilution.

Parenteral application of the compositions of this invention can be carried out, for example as a solution formulation comprising the active in an acceptable solvent such as diethlyene glycol monoethyl ether, PEG, glycerol formal, NMP, ethyl lactate, dimethyl isosorbide, isopropylidene glycerol dimethyl sulfoxide, tetraglycol/glycufurol, water, water-solvent mixtures, ethyl oleate, medium chain triglycerides or propylene glycol dicaprylate/dicaprate, or mixtures thereof; additional excipients such as surfactants, solubiliziers, complexation agents such as cyclodextrin-derivatives, suitable preservatives and/or stabilizing agents may be added. As a parenteral suspension formulation the active will be dispersed in its crude, micronized or nanosized form in an acceptable carrier solvent such as water, a water-solvent mixture or an oily carrier such as a natural/vegetable oil or a processed natural/vegetable oil such as castor oil, sesame oil, cottonseed oil or soybean oil, isopropylmyristate, propylene glycol dicaprylate/dicaprate, medium chain triglyceride or ethyl oleate; suitable wetting and/or thickening agents, preservatives and/ or stabilizing agents may be added. The active can also be incorporated into a parenteral emulsion or microemulsion formulation. To prolong the biological effect and release of the active suitable depot formulation, technologies can be used, such as implants or injectable depot formulations based on a polylactic acid (PLA), a poly(lactic-co-glycolic acid) PLA/PLGA, a block copolymer of PLGA and polyethylene glycol (PEG), poly-ε-caprolactone (PCL), a block copolymer of PCL with PLA, PLGA or PEG, a polyphosphester, a polyanhydride, a polyorthoester, a PEG, a PEG/cyclodextrin copolymer, a polyacrylic acid (PAA)/PEG copolymer, a poly (methacrylic acid) (PMA), sucrose or a derivative thereof, for example sucrose acetate or isobutyrate, a carbopol, a dextrane, a carboxymethyl cellulose (CMC), a chitosan, an alginate, a poloxamer, a hyaluronate or a polyethylene carbonate.

The antiparasitic compositions of this invention normally comprise 0.1 to 100%, preferably 0.1 to 95%, of active substance and 1 to 99.9%, preferably 5 to 99.9%,—at least—of a solid or liquid adjuvant, 0 to 25%, preferably 0.1 to 20%, of the composition preferably being surfactants (%=percent by weight). While concentrated compositions are sometimes preferred as commercial goods, the end user, e.g. for bath application, normally uses compositions which are diluted with water and which have a substantially lower active substance content.

For example, in case of a bath treatment a concentration of from 0.001 to 50 ppm, preferably 0.005 to 20 ppm and in particular 0.005 to 10 ppm, based on the entire bath, of active ingredient of the formula (I) above) has turned out to be advantageously. In addition, the concentration of the active substance during application depends on the manner and duration of treatment and also on the age and condition of the fish so treated. A typical bath treatment time is from 15 minutes to 4 hours, in particular from 30 minutes to 1 hour. The bath can contain further adjuvants, such as stabilizers, antifoams, viscosity regulators, binders, tackifiers as well as other active substances for achieving special effects. Preferred compositions to be added to the bath are, in particular, composed as follows: (%=percent by weight, based on the entire formulation):

Emulsifiable Concentrates:
active substance: 1 to 90%, preferably 5 to 20%
surfactant: 1 to 30%, preferably 10 to 20%
solvent: 5 to 98%, preferably 70 to 85%
Suspension Concentrates:
active substance: 5 to 75%, preferably 10 to 50%
water: 94 to 24%, preferably 88 to 30%
surfactant: 1 to 40%, preferably 2 to 30%
Wettable Powders:
active substance: 0.5 to 90%, preferably 1 to 80%
surfactant: 0.5 to 20%, preferably 1 to 15%
solid carrier: 5 to 99%, preferably 15 to 98%
Granulates:
active substance: 0.5 to 30%, preferably 3 to 15%
solid carrier: 99.5 to 70%, preferably 97 to 85%

Further preparation formulations for the bath application are, for example, the following emulsifiable concentrates, solutions, granulates or suspension concentrates:

FORMULATION EXAMPLES

%=Percent by Weight, Based on the Entire Formulation

| Example F1 | | | |
|---|---|---|---|
| Emulsifiable concentrates | a) | b) | c) |
| active substance | 5% | 10% | 20% |
| sorbitan laurate 30% | 30% | 30% | 6% |
| diethylene glycol monoethyl ether | 15% | 25% | 25 |
| Medium chain triglycerides | 15% | 15% | 5 |
| n-methyl-2-pyrrolidone | 10% | 20% | 20% |
| ethanol | 25% | —% | —% |

Emulsions of any required concentration can be produced from such concentrates by dilution with water.

| Example F2 | | | | |
|---|---|---|---|---|
| Solutions | a) | b) | c) | d) |
| active substance | 15% | 5% | 20% | 1% |
| diethylene glycol monomethyl ether | 80% | — | — | — |
| polyethylene glycol MG 300 | — | 75% | — | — |
| N-methyl-2-pyrrolidone | — | 20% | — | — |

-continued

Example F2

| Solutions | a) | b) | c) | d) |
|---|---|---|---|---|
| propylene glycol dicaprylate/dicaprate | 5% | — | — | 99% |
| DMSO | — | — | 80% | — |

These solutions are suitable for application in the form of microdrops.

Example F3

| Granulates | a) | b) | c) | d) |
|---|---|---|---|---|
| active substance | 5% | 10% | 8% | 21% |
| kaolin | 94% | — | 79% | 54% |
| highly dispersed silicic acid | 1% | — | 13% | 7% |
| attapulgite | — | 90% | — | 18% |

The active substance is dissolved in dichloromethane, the solution is sprayed onto the carrier, and the solvent is subsequently removed by evaporation under vacuum.

Example F4

| suspoemulsion | |
|---|---|
| active substance | 10% |
| polysorbate 80 | 12% |
| sorbitan sesquioleate | 8% |
| Mineral oil | 30% |
| water | 50% |

Emulsions of any required concentration can be produced from such concentrates by dilution with water.

Example F5

| Extruder granulate | |
|---|---|
| active substance | 10% |
| sodium ligninsulfonate | 2% |
| carboxymethyl cellulose | 1% |
| kaolin | 87% |

The active substance is mixed with the adjuvants and the mixture is ground and moistened with water. This mixture is extruded, granulated and then dried in a stream of air.

Example F6

| Coated granulates | |
|---|---|
| active substance | 3% |
| polyethylene glycol (MG 200) | 3% |
| kaolin | 94% |

The finely ground active substance is uniformly applied, in a mixer, to the kaolin moistened with polyethylene glycol. Non-dusty coated granulates are obtained in this manner.

Example F7

| Suspension concentrate | |
|---|---|
| active substance | 20% |
| ethanol | 2% |
| polysorbate 20 | 10% |
| sodium carboxymethyl cellulose | 3% |
| BHT | 0.2% |
| antifoam emulsion | 2% |
| water | 62.8% |

The finely ground active substance is homogeneously mixed with the adjuvants, giving a suspension concentrate from which suspensions of any desired concentration can be obtained by dilution with water.

Formulations suitable as feed additive are, for example, those comprising from 0.1 to 100%, preferably from 0.1 to 50%, and in particular from 0.5 to 10% by weight of active ingredient of the formula (I) and further excipients ad 100% by weight. Suitable excipients of the feed additives are, for example, starches, such as maize starch, partially or fully gelatinized starch, celluloses, such as hydroxypropyl cellulose (HPC), hydroxypropylmethyl cellulose (HMPC), silicon dioxides, gelatines, oils, such as fish oil, preservatives, such as benzyl alcohol, and water or aqueous solvent systems such as water/alcohol.

Suitable feed additives are composed e.g. as follows (%=percent by weight, based on the entire formulation):

| a) | active substance: | 0.1 to 100% |
|---|---|---|
| | maize starch: | 0 to 99% |
| | gelatin: | 0 to 10% |
| | colloidal silicon dioxide: | 0 to 10% |
| b) | active substance: | 0.5 to 10% |
| | benzyl alcohol: | 0.08 to 1.4% |
| | hydroxypropylmethyl cellulose: | 0 to 3.5% |
| | water: | ad 100% |
| c) | active substance | 0.1 to 50% |
| | fish oil | ad 100% |

The present invention also concerns a feedstuff comprising one or more compounds of the formula (I) as described above including all definitions and preferences contained therein.

The present invention also concerns a liquid formulation of a compound of formula (I) useful as injectables into fish for the curative or preferably prophylactic treatment against sea lice. Particularly interesting is the use of antiparasitically active substances of the formula I in admixture with vaccine components, for the manufacture of a composition that gives active immunological protection against bacterial or viral diseases as well as conferring prophylactic protection against sea lice. Combining vaccine and prophylactic treatment in one product results in protection against bacterial, viral and/or parasitic diseases. The advantage of such a product is that it will neither cause additional stress to the fish nor additional workload for the fish farmer, because the use of injection vaccines against bacterial and viral diseases is already well established in the fish farming industry.

As injection preparations according to the invention, the compound of the formula I is normally not applied in pure form, but preferably in the form of a composition or preparation which contains, in addition to the active ingredient, application-enhancing constituents or formulation excipients, whereby such constituents are beneficial to the fish. In general, beneficial constituents are the formulation excipients for injection preparations which are physiologically tolerated by humans and animals and are known from pharmaceutical chemistry.

Such injection compositions or preparations to be used according to the invention usually contain 0.1 to 99% by weight, especially 0.1 to 95% by weight, of a compound of formula I, and 99.9 to 1% by weight, especially 99.9 to 5% by weight, of a liquid, physiologically acceptable excipient, including 0 to 25% by weight, especially 0.1 to 25% by weight, or a non-toxic surfactant and water. Especially preferred injectable preparations contain from 0.1 to 15% by weight, preferably 0.5 to 15% by weight, and in particular 1 to 10% by weight of a compound of formula (I), each based on the entire formulation, the remainder being, for example surfactants such as those mentioned before, and solvents such as water, NMP, low molecular polyethylene glycols, DMSO, glycerol formal, propylene glycol, dicaprylate/dicaprate, vegetable oils, ethyl oleate and the like.

Whereas it is preferred to formulate commercial products as a ready-to-use injection formulation, it is also possible to employ a concentrated formulation or solid formulation of a compound of formula (I) which is diluted or reconstituted by the end user before use.

The formulations suitable for injection are for example aqueous solutions of the active ingredients in water-soluble form, e.g. a water-soluble salt, in the broader sense also suspensions of the active ingredients, such as appropriate oily injectable suspensions, whereby e.g. to delay the release of active ingredient (slow release), suitable lipophilic solvents or vehicles are used, such as oils, e.g. sesame oil, or synthetic fatty acid esters, e.g. ethyl oleate, or triglycerides, or aqueous injectable suspensions containing viscosity-increasing agents, e.g. sodium carboxymethyl cellulose, sorbitol and/or dextran, and where appropriate stabilizers. Oil-containing formulations with delayed release of active ingredient are called depot preparations here and hereinafter, and they belong to the preferred embodiments of the present invention, since, especially in the case of prophylactic administration, they are able to protect the fish for long periods from an infestation by the sea lice.

Injectable compositions according to the invention can be formulated as a solution, suspension or emulsion of the antiparasitically active substance of the formula I, with or without vaccine components.

One preferred embodiment of the present invention is a composition for controlling sealice, characterized in that it is formulated as an injectable formulation containing as active principle either a compound of the formula I or a combination of a compound of the formula I together with vaccine component.

EXAMPLES OF INJECTION FORMULATIONS

| Example F8 | |
|---|---|
| non-aqueous injection formulation. | |
| active ingredient | 20.0 mg |
| NMP | 200 mg |
| PEG 300 | ad 1.0 ml |

| Example F9 | |
|---|---|
| non-aqueous injection formulation based on oil | |
| active ingredient | 10 mg |
| NMP | 200 mg |
| medium chain triglycerides | ad 1.0 ml |

| Example F11 | |
|---|---|
| Active ingredient | 20 mg |
| Polysorbate 80 | 50 mg |
| PEG 300 | ad 1.0 ml |

| Example F12 | | | |
|---|---|---|---|
| | a) | b) | c) |
| Active ingredient | 5% | 5% | 5% |
| DMSO | ad 100 | | |
| Diethylene glycol monoethyl ether | | | ad 100 |
| Glycerol formal | | ad 100 | |

| Example F13 | |
|---|---|
| Injectables with delayed release of active ingredient | |
| Oily vehicles (slow release) | |
| active ingredient | 0.1-5.0 g |
| propylene glycol dicaprylate/dicaprate or | ad 100 ml |
| active ingredient | 0.1-1.0 g |
| sesame oil | ad 100 ml |

The active ingredient is dissolved in part of the oil or excipient mixture whilst stirring and, if required, with gentle heating, then after cooling made up to the desired volume and sterile-filtered through a suitable membrane filter with a pore size of 0.22 μm.

| Example F14 | | | |
|---|---|---|---|
| in-situ forming depots | | | |
| a) Lactide/Caprolactone copolymers | | | |
| Active ingredient | 0.1-10% | 0.1-10% | 0.1-10% |
| DMSO | ad 100 | | |
| Diethlyene glycol monoethyl ether | | ad 100 | |
| Tetraglycol | | | ad 100 |
| PLA/PCL copolymer | 0.1-50% | 0.1-50% | 0.1-50% |
| b) PLA/PEG copolymers | | | |
| Active ingredient | 0.1-10% | 0.1-10% | |
| DMSO | ad 100 | | |
| Diethylene glycol monoethyl ether | | ad 100 | |
| PLA/PEG copolymer | 0.1-50% | 0.1-50% | |

| Example F15 | |
|---|---|
| Further injection formulations | |
| 15a: Aqueous suspension | |
| active ingredient (micronized) | 1-5 g |
| povidone | 5 g |
| sodium chloride | 0.9 g |
| phosphate buffer solution | 10 g |
| benzyl alcohol | 2 g |
| water for injection | ad 100 ml |
| 15b: Solubilisate | |
| active ingredient | 0.1-0.5 g |
| polyethylene glycol-15-hydroxystearate | 15 g |

| Example F15 | |
|---|---|
| Further injection formulations | |
| propylene glycol | 65 g |
| benzyl alcohol | 4 g |
| water for injection | ad 100 ml |
| 15c: Oily suspension | |
| active ingredient (micronized) | 1-5 g |
| ethyl oleate | ad 100 ml |

Table 1 presents a list of compounds according to the invention, which are particularly well applicable in these formulations.

| Example | Structure |
|---|---|
| 1 | *(3,5-dichlorophenyl isoxazoline with trifluoromethyl, linked to methyl-phenyl-triazole)* |
| 2 | *(3,5-dichlorophenyl isoxazoline with trifluoromethyl, linked to methyl-benzamide with N-(pyridin-2-ylmethyl))* |
| 3 | *(3,5-dichlorophenyl isoxazoline with trifluoromethyl, linked to methyl-benzamide with N-(2,2,2-trifluoroethyl))* |
| 4 | *(3,5-dichlorophenyl isoxazoline with trifluoromethyl, linked to methyl-phenyl-pyrazole)* |
| 5 | *(3,5-dichlorophenyl isoxazoline with trifluoromethyl, linked to methyl-phenyl-imidazole)* |

| Example | Structure |
|---|---|
| 6 | 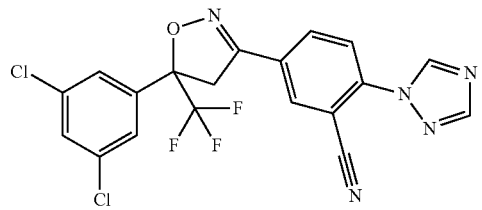 [SMILES: N#Cc1cc(C2=NOC(c3cc(Cl)cc(Cl)c3)(C(F)(F)F)C2)ccc1-n1cncn1] |
| 7 | 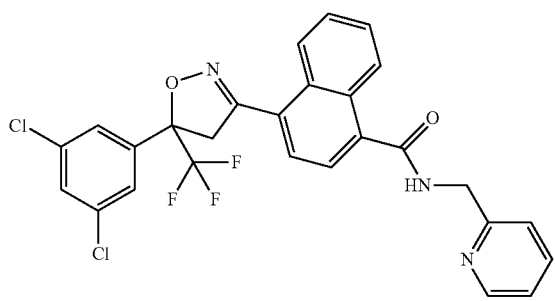 [SMILES: O=C(NCc1ccccn1)c1ccc(C2=NOC(c3cc(Cl)cc(Cl)c3)(C(F)(F)F)C2)c2ccccc12] |
| 8 | 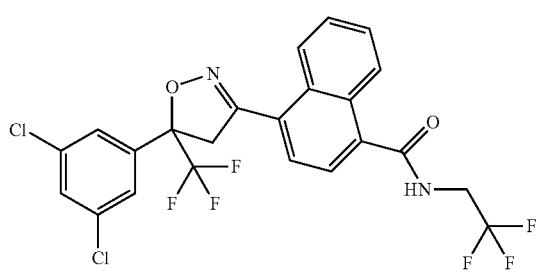 [SMILES: O=C(NCC(F)(F)F)c1ccc(C2=NOC(c3cc(Cl)cc(Cl)c3)(C(F)(F)F)C2)c2ccccc12] |
| 9 | 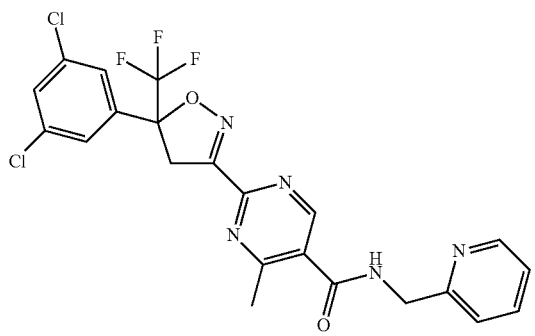 [SMILES: Cc1nc(C2=NOC(c3cc(Cl)cc(Cl)c3)(C(F)(F)F)C2)ncc1C(=O)NCc1ccccn1] |
| 10 | 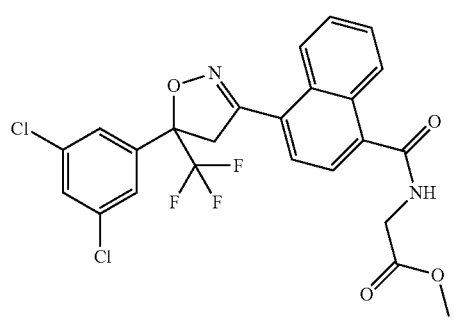 [SMILES: COC(=O)CNC(=O)c1ccc(C2=NOC(c3cc(Cl)cc(Cl)c3)(C(F)(F)F)C2)c2ccccc12] |

-continued

| Example | Structure |
|---|---|
| 11 | 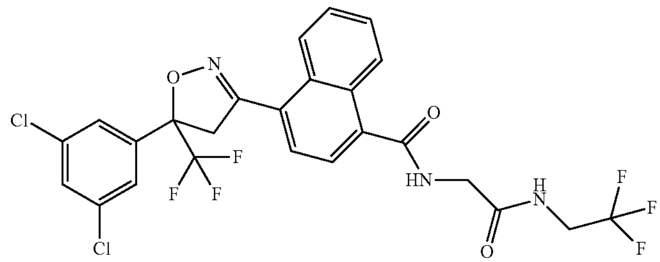 [SMILES: O=C(CNC(=O)c1ccc(C2=NOC(c3cc(Cl)cc(Cl)c3)(C(F)(F)F)C2)c2ccccc12)NCC(F)(F)F] |
| 12 | 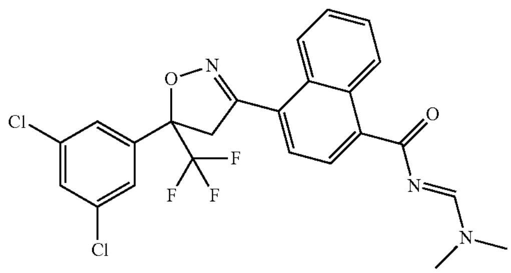 [SMILES: CN(C)/C=N/C(=O)c1ccc(C2=NOC(c3cc(Cl)cc(Cl)c3)(C(F)(F)F)C2)c2ccccc12] |
| 13 | 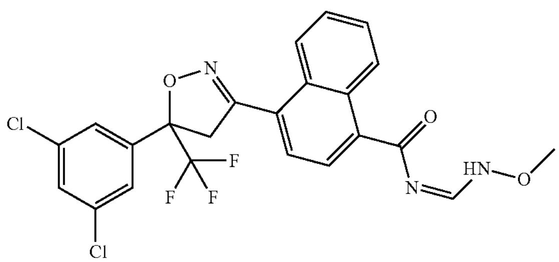 [SMILES: CON/C=N\C(=O)c1ccc(C2=NOC(c3cc(Cl)cc(Cl)c3)(C(F)(F)F)C2)c2ccccc12] |
| 14 | 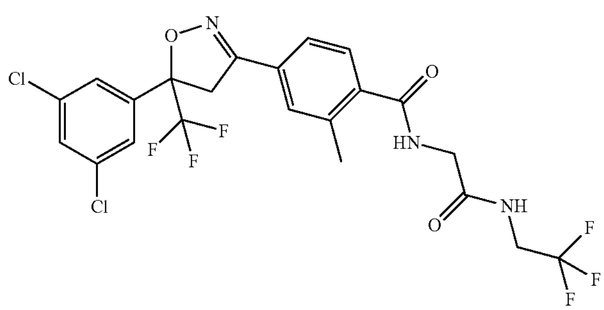 [SMILES: Cc1cc(C2=NOC(c3cc(Cl)cc(Cl)c3)(C(F)(F)F)C2)ccc1C(=O)NCC(=O)NCC(F)(F)F] |
| 15 | 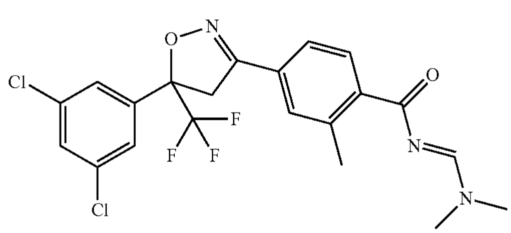 [SMILES: Cc1cc(C2=NOC(c3cc(Cl)cc(Cl)c3)(C(F)(F)F)C2)ccc1C(=O)/N=C/N(C)C] |
| 16 | 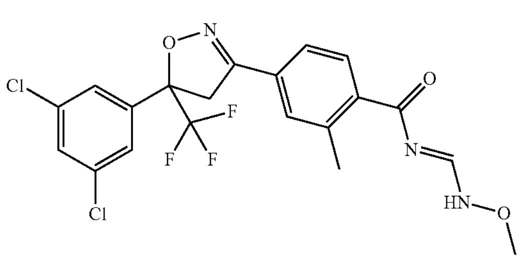 [SMILES: CON/C=N/C(=O)c1ccc(C2=NOC(c3cc(Cl)cc(Cl)c3)(C(F)(F)F)C2)cc1C] |

| Example | Structure |
|---|---|
| 17 | 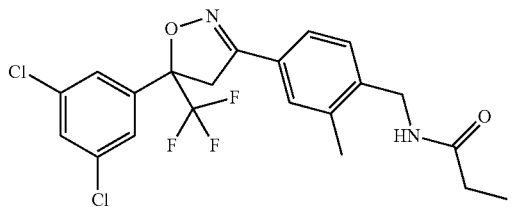 [SMILES: CCC(=O)NCc1ccc(C2=NOC(c3cc(Cl)cc(Cl)c3)(C(F)(F)F)C2)cc1C] |
| 18 | 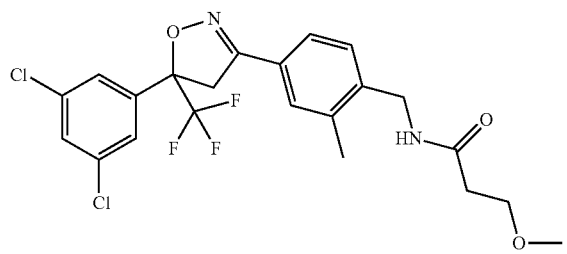 [SMILES: COCCC(=O)NCc1ccc(C2=NOC(c3cc(Cl)cc(Cl)c3)(C(F)(F)F)C2)cc1C] |
| 19 | 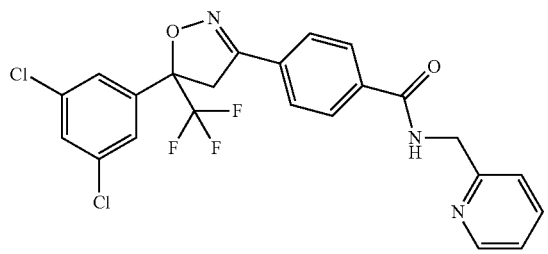 [SMILES: O=C(NCc1ccccn1)c1ccc(C2=NOC(c3cc(Cl)cc(Cl)c3)(C(F)(F)F)C2)cc1] |
| 20 | 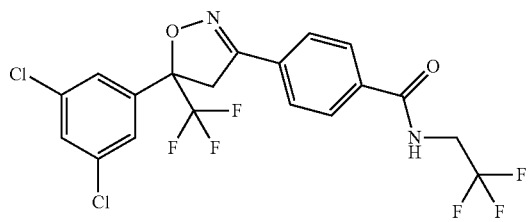 [SMILES: O=C(NCC(F)(F)F)c1ccc(C2=NOC(c3cc(Cl)cc(Cl)c3)(C(F)(F)F)C2)cc1] |
| 21 | 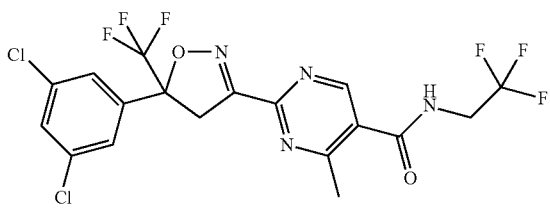 [SMILES: Cc1nc(C2=NOC(c3cc(Cl)cc(Cl)c3)(C(F)(F)F)C2)ncc1C(=O)NCC(F)(F)F] |
| 22 | 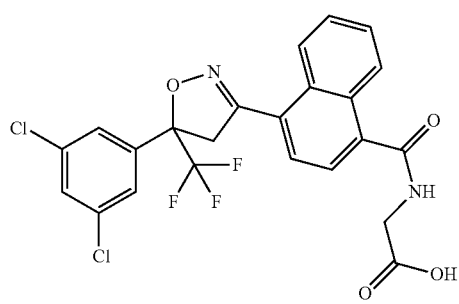 [SMILES: O=C(O)CNC(=O)c1ccc(C2=NOC(c3cc(Cl)cc(Cl)c3)(C(F)(F)F)C2)c2ccccc12] |

-continued

| Example | Structure |
|---|---|
| 23 | (chemical structure) |
| 24 | (chemical structure) |
| 25 | (chemical structure) |
| 26 | (chemical structure) |
| 27 | (chemical structure) |
| 28 | (chemical structure) |
| 29 | (chemical structure) |

| Example | Structure |
|---------|-----------|

30

31

32

33

BIOLOGICAL EXAMPLES

Activity in Vitro Against *Lepeophtheirus Salmonis* at Copepodid Stage

Sea lice copepodids were used to seed a 96-well plate containing the test substances to be evaluated for antiparasitic activity. Each compound was tested by serial dilution in order to determine its minimal effective dose (MED). Copepodids were left in contact with the test compound diluted in sea water for 1 hour. They were then incubated in untreated sea water for 48 h. Efficacy against sea lice was then confirmed if no copepodid moved over a period of 80 seconds.

In this test the following examples showed efficacy (EC80) at 50 ppb: 1, 2, 3, 6, 7, 8, 10, 11, 12, 13, 14, 16, 17, 18, 24, 25, 26, 27, 28, 29, 30, 31, 33.

In Vitro Activity of Compound 8 Against *Lepeophtheirus Salmonis* at Adult Stage Ten mixed sex adult lice (non gravid, *Lepeophtheirus salmonis*) were removed from fish and exposed to a test compound at several dilution in filtered sea water and placed in an incubator at 12° C. in dark conditions. After 60 minutes exposure, lice were rinsed in clean sea water and transferred to petri dishes containing 100 mL of sea water. They were then returned to the incubator. Lice were examined for survival at 24 hours post exposure (moribund lice considered as dead)

In this test compound 8 showed more than 90% efficacy at 1 ppm.

In Vivo Activity of Compound 8 Against *Lepeophtheirus Salmonis* on Atlantic Salmon using Injectable Application Twenty Atlantic salmon (mean weights at about 100 g) were anaesthetized with 2-phenoxy ethanol, individually weighed and injected with 0.2 ml of compound 8 formulated in PEG300 at 2.5%, corresponding to a 50 mg/kg dose. Each treatment was administered by single IP injection and fish were then transferred to a flow through tank, the temperature of which was maintained between 6 and 14° C. Louse infection was by exposure of experimental fish to louse copepodids freshly hatched from *Lepeophtheirus salmonis* egg strings. The number of copepodids used was selected to provide a settlement rate of at least 10 lice per fish. Sea louse numbers were assessed when they had developed to chalimus stage III/IV or later on if needed.

Ten fish per group were anaesthetized with 2 phenoxy-ethanol and examined for louse settlement under a dissecting microscope. Differences in sea louse counts between each test group and the relevant control group (non treated) infested at the same time as the test group were assessed using Mann-Whitney Tests. Efficacy was calculated using the formula:

% Efficacy=100−(100×mean of treatment group/mean of control).

As depicted in the table below, compound 8 showed more than 90% efficacy for up to 7 months post treatment.

| Days post treatment | Predominant stage of lice | Mean lice count of treated fish ± s.d. | Mean lice count of control fish ± s.d. | Efficacy |
|---|---|---|---|---|
| 14 | Chalimus III | 0.1 ± 0.3 | 18.2 ± 9.3 | 99.5% |
| 41 | Chalimus III | 0.0 ± 0.0 | 43.3 ± 26.0 | 100% |
| 83 | Chal III/IV | 0.0 ± 0.0 | 22.7 ± 12.8 | 100% |
| 127 | Chal III/IV | 0.0 ± 0.0 | 25.7 ± 8.4 | 100% |
| 169 | Chal III/IV | 0.0 ± 0.0 | 29.9 ± 23.9 | 100% |
| 217 | Chal III/IV | 22.9 ± 27.7 | 89.2 ± 49.3 | 74.3% |
|  | PAI & PAII | 4.5 ± 5.8 | 82.7 ± 26.1 | 94.6% |
|  | Adults | 0.5 ± 1.0 | 18.2 ± 5.2 | 97.3% |
| 252 | Chal IV/PAI | 21.4 ± 15.5 | 30.5 ± 10.1 | 29.8% |
|  | Adults | 4.0 ± 216 | 26.5 ± 8.0 | 84.9% |

In Vivo Activity of Compound 8 Against *Lepeophtheirus Salmonis* on Atlantic Salmon using Bath Treatment Application Bath containing compound 8 at 2 ppm in salt water was prepared by dilution of a solution of compound 8 in DMSO. Fish (Atlantic salmons) had been previously infected with 2 cohorts of lice to ensure the presence of chalimus and motile lice at the time of treatment. This test was performed on thirty fish per group and was compared to 30 control fish that were bathed in sea water containing DMSO only (at an inclusion rate equal to that used in the test group using the most DMSO as solvent), for 60 minutes. The fish were then transferred to holding tanks and sampled for lice numbers at 3 and 10 days post treatment.

Ten fish per group were anaesthetized with 2 phenoxy-ethanol and examined for louse settlement under a dissecting microscope. Differences in sea louse counts between each test group and the relevant control group (non treated) infested at the same time as the test group were assessed using Mann-Whitney Tests. Efficacy was calculated using the formula:

% Efficacy=100−(100×mean of treatment group/mean of control).

In this test compound 8 was found to be 100% effective against adult sea lice at 3 days post treatment and 96% effective against developing chalimus stage by 10 days post treatment.

In Vivo Activity of Compound 8 Against *Lepeophtheirus Salmonis* on Atlantic Salmon using In-Feed Application Compound 8 was administered orally via medicated fish pellets at an average dose of 9.8 mg/kg/day during 7 consecutive days to 50 Atlantic salmon infected with lice (*Lepeophtheirus salmonis*). The medicated pellets were prepared by dry top coating of the compound 8, formulated as feed additive as described above, and over-oiling to seal (1% fish oil). Fish had been previously infected by exposure to louse. The number of copepodids used was selected to provide an settlement rate of at least 10 lice per fish. Treatment was done when lice had developed to pre-adult II and adult stages. Sea louse numbers were assessed 34 days post treatment. A second challenge using louse copepodids took place at 41 days post treatment. Sea louse numbers were assessed when they had developed to adults.

All fish were anaesthetized with 2 phenoxy-ethanol and examined for louse settlement under a dissecting microscope. Differences in sea louse counts between each test group and the relevant control group (non treated) infested at the same time as the test group were assessed using Mann-Whitney Tests. Efficacy was calculated using the formula:

% Efficacy=100−(100×mean of treatment group/mean of control).

In this test, compound 8 was found to be 100% as a curative treatment (first challenge) and also showed 100% on the challenge performed 41 days post treatment.

What is claimed:

1. A method of controlling sea lice in and on fish, which comprises treating the sea lice by an in-feed treatment, wherein an active substance is added to the feed provided to the fish, said active substance being a compound of formula

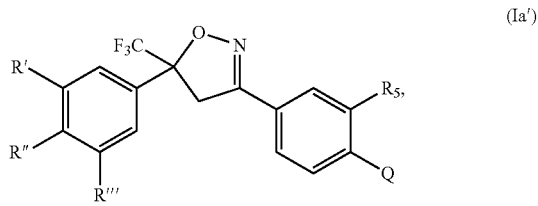

(Ia')

or

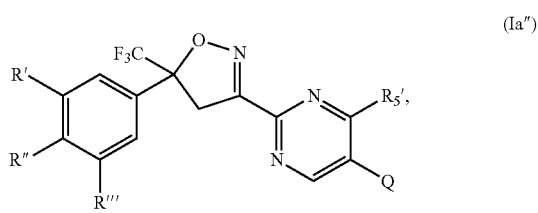

(Ia")

wherein R', R" and R'" are each H, halogen or trifluormethyl, subject to the proviso that at least one of R', R" and R'" is not H;

R$_5$ is methyl, halogen, CF$_3$ or cyano;

Q is a radical selected from the group consisting of:

(q1)

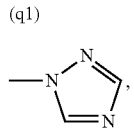

(q2)

—C(O)NH—CH$_2$CF$_3$, (q3)

(q4)

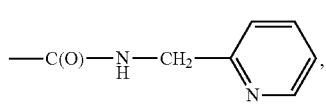

(q5)

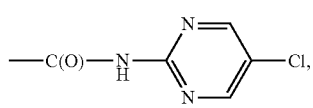

(q6) 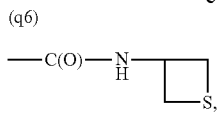

(q7) 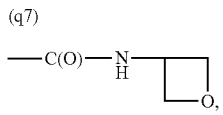

(q8) —C(O)NH—CH$_2$—C(O)NH—CH$_2$CF$_3$,
(q9) —C(O)NH—CH$_2$—C(O)NH—CH$_2$CN,
(q10) —C(O)NH—CH$_2$—C(O)NH—CH$_2$C≡CH,
(q11) —C(O)NH—C≡N—O—CH$_3$,
(q12) —C(O)N═C—N(CH$_3$)$_2$,
(q13) —C(O)N═C(NH$_2$)—O—CH$_3$,
(q14) —CH$_2$—NH—C(O)—C$_1$-C$_3$-alkyl,
(q15) —CH$_2$—NH—C(O)-cyclopropyl,
(q16) —CH$_2$—NH—C(O)—C$_1$-C$_2$-haloalkyl,
(q17) —CH$_2$—NH—C(O)—CH$_2$—S—C$_1$-C$_2$-alkyl,
(q18) —CH$_2$—NH—C(O)—CH$_2$—S(O)$_2$—C$_1$-C$_2$-alkyl, and
(q19) —CH$_2$—NH—C(O)—(CH$_2$)$_{1-2}$—O—C$_1$-C$_2$-alkyl;
and wherein Q' is a radical (q2) to (q19) above.

2. A method according to claim 1, wherein R' and R"40 are each independently of the other chlorine and R" is H.

3. A method according to claim 1, wherein the active substance is of formula (Ia').

4. A method according to claim 1, wherein the active substance is of formula (Ia''').

5. A method according to claim 1, wherein the fish are of the Salmonidae family.

6. A method according to claim 1, wherein the sea lice are of the Copepodae class.

7. A method according to claim 3, wherein the active substance is of formula

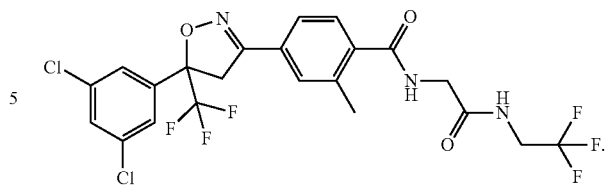

8. A method according to claim 4, wherein the active substance is of formula

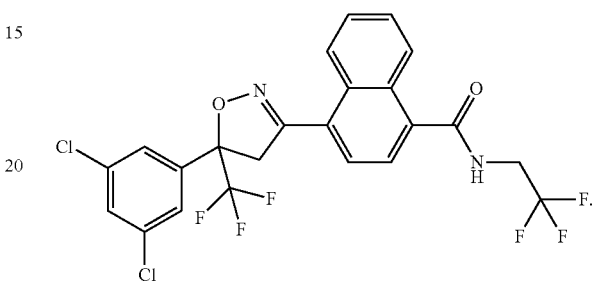

9. A method according to claim 5, wherein the fish are selected from the group consisting of *Salmo salar, Salmo trutta, Oncorhynchus mykiss, Oncorhynchus gorbuscha, Oncorhynchus keta, Oncorhynchus nekra, Oncorhynchus kisutch, Oncorhynchus tshawytscha, Oncorhynchus mamson, Salvelinus* species and *Salmo clarkii*.

10. A method according to claim 6, wherein the sea lice are selected from the group consisting of *Lepeophtheirus salmonis, Caligus elongatus* and *C. rogercresseyii*.

* * * * *

UNITED STATES PATENT AND TRADEMARK OFFICE
CERTIFICATE OF CORRECTION

PATENT NO. : 9,023,836 B2
APPLICATION NO. : 13/805206
DATED : May 5, 2015
INVENTOR(S) : Jean-Luc Perret et al.

It is certified that error appears in the above-identified patent and that said Letters Patent is hereby corrected as shown below:

IN THE CLAIMS

At Column 42, Line 15-36, In Claim 1,

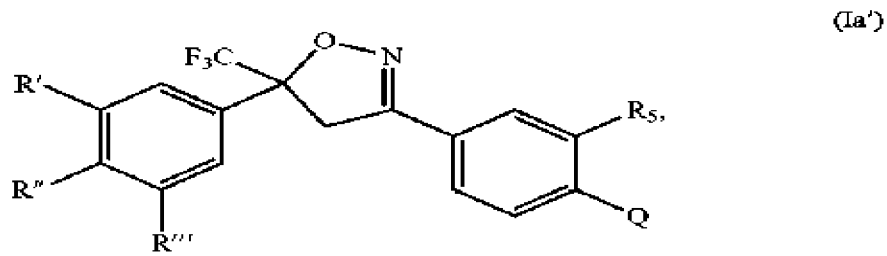
(Ia')

or

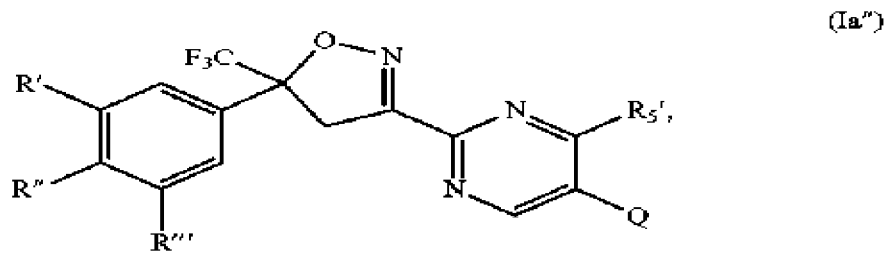
(Ia")

delete " " and

Signed and Sealed this
Twenty-fourth Day of November, 2015

Michelle K. Lee
*Director of the United States Patent and Trademark Office*

CERTIFICATE OF CORRECTION (continued)
U.S. Pat. No. 9,023,836 B2 insert -- 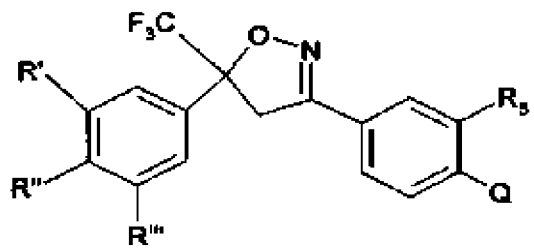 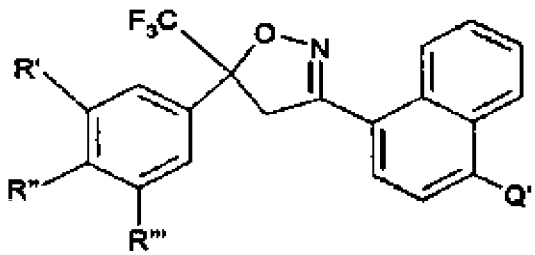 --, therefor.

At Column 42, Line 37-38, In Claim 1, delete "trifluormethyl," and insert -- trifluoromethyl, --, therefor.

At Column 43, Line 25, In Claim 2, delete "R″40" and insert -- R‴ --, therefor.

At Column 44, Line 30, In Claim 9, delete "nekra," and insert -- nerka, --, therefor.

At Column 44, Line 35, In Claim 10, delete "rogercresseyii" and insert -- rogercresseyi, --, therefor.